US012637687B2

(12) United States Patent
Kong et al.

(10) Patent No.: US 12,637,687 B2
(45) Date of Patent: *May 26, 2026

(54) NUCLEIC ACID MOLECULES, POLYPEPTIDES HAVING EPOXY GROUP-REMOVING CATALYTIC ACTIVITY AND USE THEREOF

(71) Applicant: SHANDONG AGRICULTURAL UNIVERSITY, Taian City (CN)

(72) Inventors: Lingrang Kong, Taian City (CN); Hongwei Wang, Taian City (CN); Silong Sun, Taian City (CN); Wenyang Ge, Taian City (CN); Bingqian Hou, Taian City (CN)

(73) Assignee: SHANDONG AGRICULTURAL UNIVERSITY, Taian City (CN)

( * ) Notice: Subject to any disclaimer, the term of this patent is extended or adjusted under 35 U.S.C. 154(b) by 351 days.

This patent is subject to a terminal disclaimer.

(21) Appl. No.: 17/905,591

(22) PCT Filed: Dec. 11, 2020

(86) PCT No.: PCT/CN2020/135821
§ 371 (c)(1),
(2) Date: Sep. 2, 2022

(87) PCT Pub. No.: WO2021/174949
PCT Pub. Date: Sep. 10, 2021

(65) Prior Publication Data
US 2023/0063483 A1 Mar. 2, 2023

(30) Foreign Application Priority Data

Mar. 5, 2020 (CN) ........................ 202010146399.X
Mar. 5, 2020 (CN) ........................ 202010146400.9

(51) Int. Cl.
*C12N 15/82* (2006.01)
*A23L 2/84* (2006.01)
(Continued)

(52) U.S. Cl.
CPC ............ *C12N 15/8282* (2013.01); *A23L 2/84* (2013.01); *A23L 5/25* (2016.08); *C12N 9/0004* (2013.01);
(Continued)

(58) Field of Classification Search
None
See application file for complete search history.

(56) References Cited

PUBLICATIONS

Wahibah, N. N., Tsutsui, T., Tamaoki, D., Sato, K., & Nishiuchi, T. (2018). Expression of barley Glutathione S-Transferase 13 gene reduces accumulation of reactive oxygen species by trichothecenes and paraquat in *Arabidopsis* plants. Plant Biotechnology, 35(1), 71-79. (Year: 2018).*
(Continued)

*Primary Examiner* — Amjad Abraham
*Assistant Examiner* — Dequantarius Javon Speed
(74) *Attorney, Agent, or Firm* — HAUPTMAN HAM, LLP

(57) ABSTRACT

Disclosed are a nucleic acid molecule, a polypeptide having epoxy group-removing catalytic activity and use thereof. According to the invention, by means of genetic engineering, the nucleic acid molecule encoding a de-epoxidation protein is expressed in a plant, so that an epoxy group of a trichothecene mycotoxin is removed, and the toxin amount in the plant is reduced. The polypeptide of the invention is capable of catalyzing a reaction between vomitoxin and glutathione under mild conditions to remove epoxy groups to produce a glutathionylated derivative.

3 Claims, 11 Drawing Sheets

Specification includes a Sequence Listing.

(51) Int. Cl.
     *A23L 5/20*                    (2016.01)
     *C12N 9/02*                    (2006.01)
(52) U.S. Cl.
     CPC ...... *C12N 15/8202* (2013.01); *A23V 2002/00*
                    (2013.01); *C12N 2800/10* (2013.01)

(56)                    References Cited

PUBLICATIONS

Doughari, JH. (2015). An Overview of Plant Immunity. Journal of Plant Pathol Microbiol 2015, 6:11. (Year: 2015).*

Lazar et al. (1998). Transforming growth factor alpha: mutation of aspartic acid 47 and leucine 48 results in different biological activities. Molecular Cell Biology, 8(3):1247-52. doi: 10.1128/mcb. 8.3.1247-1252. (Year: 1998).*

Nonaka et al. (2009). Truncation and pathogenic mutations facilitate the formation of intracellular aggregates of TDP-43. Human Molecular Genetics, 18(18):3353-64. (Year: 2009).*

(Y) Wang H. et al. (Apr. 9, 2020). Horizontal gene transfer of Fhb7 from fungus underlies Fusarium head blight resistance in wheat. Science, 368(6493):eaba5435. (Year: 2020).*

(Z) Hu, T., Qv, X., Xiao, G., & Huang, X. (2009). Enhanced tolerance to herbicide of rice plants by over-expression of a glutathione S-transferase. Molecular Breeding, 24, 409-418. (Year: 2009).*

Karlovsky, P.; "Biological detoxification of the mycotoxin deoxynivalenol and its use in genetically engineered crops and feed additives"; Appl Microbiol Biotechnol, Jun. 21, 2011, vol. 91, pp. 491-504.

First Office Action issued in Indian Application No. 202227050818, mailed Mar. 5, 2026, 12 pages.

Wang, Hongwei et al; "Horizontal gene transfer of Fhb7 from fungus underlies Fusarium head blight resistance in wheat"; Science, Apr. 9, 2020, 13 pages.

* cited by examiner

RT:0.00-10.02

RT:0.00-10.01

DON-GSH

DON

3-ADON-GSH

3-ADON

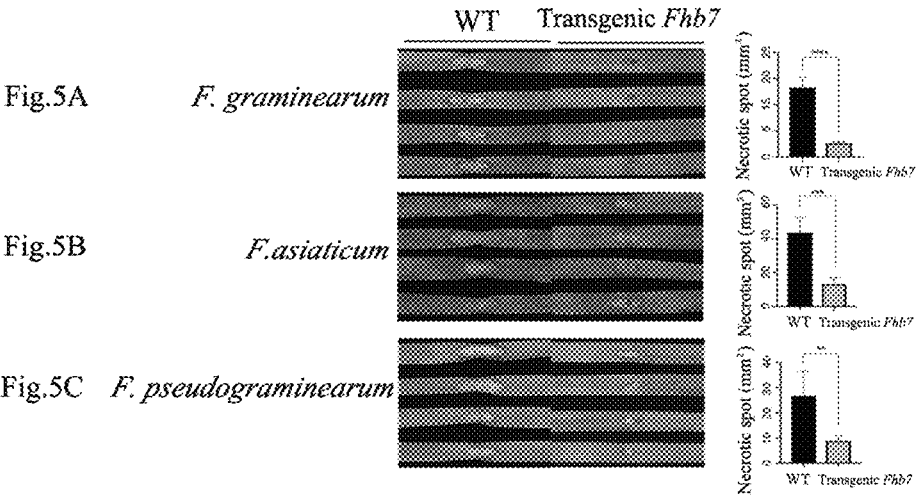
Fig.5A    *F. graminearum*
Fig.5B    *F. asiaticum*
Fig.5C    *F. pseudograminearum*
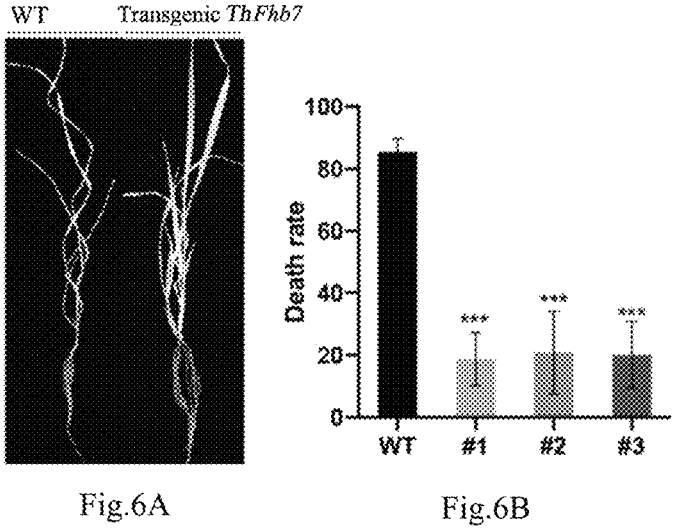
Fig.6A                    Fig.6B
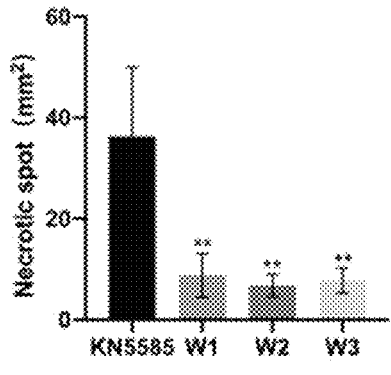
Fig.7

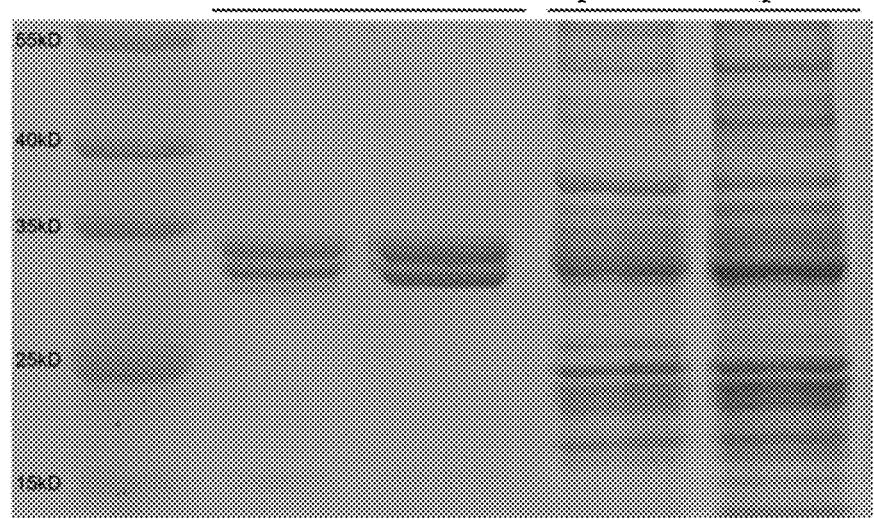
Fig.13
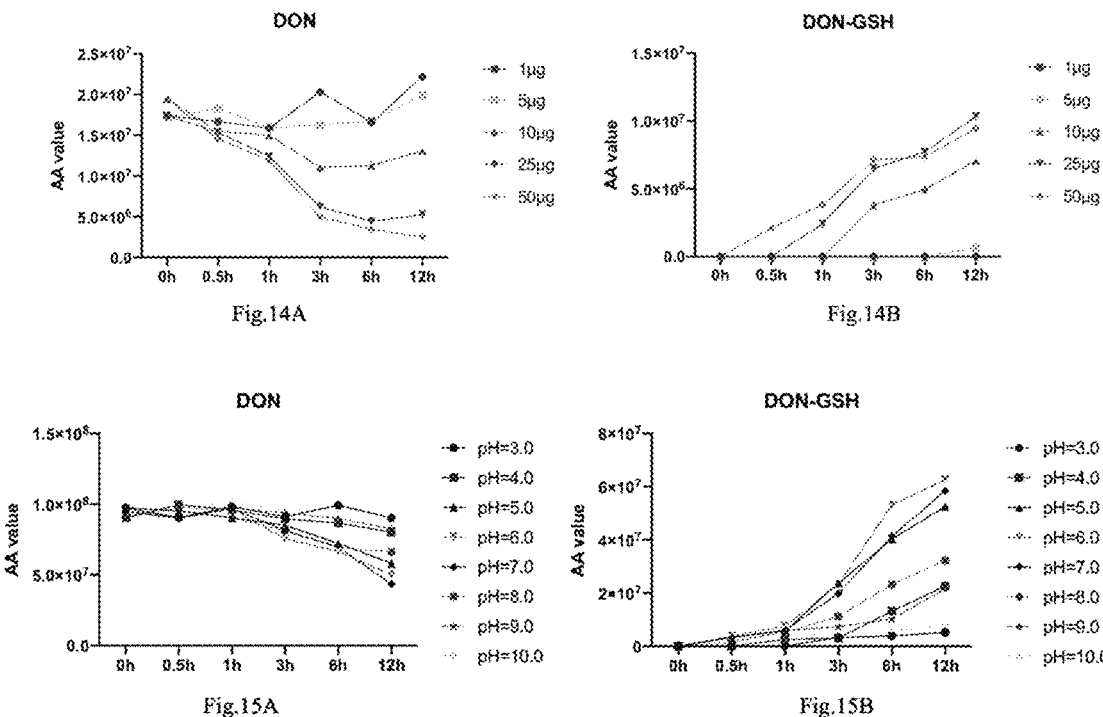
Fig.14A
Fig.14B
Fig.15A
Fig.15B

1

NUCLEIC ACID MOLECULES, POLYPEPTIDES HAVING EPOXY GROUP-REMOVING CATALYTIC ACTIVITY AND USE THEREOF

RELATED APPLICATIONS

The present application is a U.S. National Phase of International Application Number PCT/CN2020/135821 filed Dec. 11, 2020, and claims priority to Chinese Application Numbers CN 202010146400.9 and CN 202010146399.X, both filed on Mar. 5, 2020.

INCORPORATION BY REFERENCE

The sequence listing provided in the file entitled Sequence_Listing_011_v2.txt which is an ASCII text file that was created on May 20, 2024, and which comprises 47,056 bytes, is hereby incorporated by reference in its entirety.

TECHNICAL FIELD

The invention relates to the field of molecular botany, in particular to the use of a nucleic acid molecule and a polypeptide having epoxy group-removing catalytic activity in plant transgenesis, molecular breeding, disease control, molecular markers and detoxification of vomitoxin.

BACKGROUND ART

*Fusarium* sp., as a class of fungi distributed worldwide, can not only survive winter and summer in the soil, but also infect a variety of plants (such as food crops, economic crops, medicinal plants and ornamental plants), cause root rot, stem rot, stem base rot, flower rot, ear rot and other diseases of plants (more than 100 kinds of host plants), infect vascular bundle systems of host plants, destroy vascular bundles of conducting tissues of plants, and produce toxins during growth, development and metabolism to harm crops, thereby resulting in crop wilting and death, and affecting yield and quality, which is one of the most difficult and important disease-causing factors to control in production. Plants or grains infected with *Fusarium* sp. comprise a variety of mycotoxins, mainly trichothecenes (CTCs), zearalenone, butenolide, fumonisins FB, and other toxins.

The diseases caused by *F. graminearum* (mainly comprising *F. asiaticum, F. graminearum* Schwabe and *F. pseudograminearum*) infection of cereals mainly comprises Fusarium head blight and stem base rot in wheat, barley, oat, maize and millet. At present, Fusarium head blights in wheat, barley and maize are all major fungal diseases that are difficult to solve worldwide. For example, yield reduction of cereals and mycotoxin contamination in grains caused by *Fusarium* head blight in wheat have become one of the most urgent food security problems in China and the world. *F. graminearum* infects wheat ears at the flowering stage of wheat, and secretes a large amount of trichothecene mycotoxins, which significantly increases the pathogenicity of the pathogen, resulting in devastating damage to yield. Furthermore, consumption of wheat grains contaminated with this toxin can lead to loss of appetite or absolute anorexia, gastrointestinal inflammation and hemorrhage, vomiting, diarrhea, necrodermatitis, ataxia, poor blood coagulation, anemia and decreased white blood cell count, decreased immune function and miscarriage, and the like, which seriously threatens the health of humans and animals.

The vomitoxin is mainly produced by *Fusarium* sp. such as *F. graminearum, F. oxysporum, F. moniliforme, F. sporotrichioides, F. roseum, F. nivale*, and the like. In addition, strains of *Cephalosporium, Myrothecium, Trichoderma*, and the like may also produce this toxin. Ingestion of such toxin may lead to reduced feed intake and, in severe cases, for example, vomiting, and thus it is also known as vomitoxin (VT). Scientific researchers have proved that the epoxy group of vomitoxin is the main group as the source of toxicity. Therefore, isolating a gene or enzyme that can efficiently remove the epoxy group of vomitoxin, and treating toxin-contaminated cereal products through in vitro enzyme catalysis, will satisfy the needs for detoxification of vomitoxin in the feed industry, food industry and pharmaceutical industry. Unfortunately, no specific gene or protein has been reported to be capable of catalyzing the detoxification of vomitoxin by removing epoxy groups.

SUMMARY OF THE INVENTION

In view of the problems existing in the prior art, provided is a nucleic acid molecule encoding a de-epoxidation proteinic enzyme, through which the epoxy group in the toxin can be effectively removed, thereby realizing detoxification. The invention is accomplished on this basis.

A first aspect of the invention provides use of a nucleic acid molecule in plant transgenesis, molecular breeding, disease control and molecular markers, wherein the nucleic acid molecule has a sequence selected from the group consisting of the following (a) to (e):

- (a) a sequence as set forth in any of SEQ ID NOs: 1-35;
- (b) a sequence modified for the host codon bias based on the sequence of (a);
- (c) a conserved region sequence of the sequence as set forth in (a);
- (d) a sequence having 85% or more sequence identity to any of (a) to (c), and encoding a protein having epoxy group-removing catalytic activity; and
- (e) a sequence complementary to at least a portion of any of the sequences of (a) to (d).

In the sequence (a), SEQ ID NO: 1 represents a de-epoxidase gene derived from *Thinopyrum ponticum*, and SEQ ID NO: 2 represents the de-epoxidase gene derived from *Thinopyrum elongatum*. SEQ ID NOs: 3-24 represent mutants of the sequence of SEQ ID NO: 1. SEQ ID NOs: 25-35 represent homologous gene sequences derived from different species of *Epichloë*.

In the sequence (b) of the invention, the modification for the host codon bias refers to the base substitution in the sequence (a) according to codon degeneracy in order to adapt to the needs of different hosts for expression. The modification for the codon bias generally does not change the sequence of the product protein or polypeptide.

In the sequence (c), the conserved region sequence refers to a region sharing a sequence identity of 98% or more, preferably 99% or more, and more preferably 100% within corresponding sequences of different species of *Thinopyrum* and *Epichloë*. The conserved region sequence may also refer to a partially continuous region sharing a sequence identity of 100% within different species of *Thinopyrum* and may also refer to a partially contiguous region sharing a sequence identity of 100% within corresponding sequences of different species of *Epichloë*. The conserved region sequence may correspond to the conserved region sequence of amino acids of an active polypeptide. It should be noted that the conserved region sequence of bases does not necessarily express or encode an active polypeptide. As long as it is a conserved region, it can be used as a detecting target. In certain embodiments, when the sequence as set forth in SEQ ID NO: 1 is used as a position reference, the nucleic acid molecule comprises at least one sequence selected from: a sequence at positions 436-470, a sequence at positions 430-476, and a sequence at positions 808-846.

The sequence (d) is a sequence which has sequence identity of generally 85% or more, preferably 90% or more, still preferably 95% or more, more preferably 97% or more, still preferably 98% or more, further preferably 99% or more to the sequence of any of (a) to (c) and encoding a protein having epoxy group-removing catalytic activity. In general, the sequence (d) is derived from a sequence of the same genus, preferably of the same species, on the basis of the sequence identity. In certain embodiments, the sequence identity of the sequence of the nucleic acid molecule to the sequence (a), (b) or (c) is 95% or more, and all these sequences are derived from *Thinopyrum* or *Epichloë*.

The sequence (e) is a sequence complementary to at least a portion of any of the sequences of (a) to (d), wherein the complementary sequence comprises a sequence that specifically hybridizes to these sequences under stringent conditions, for example, a probe, a primer, and the like. The lengths of nucleic acid molecules or oligonucleotide molecules having these sequences are not particularly limited, and may be 15 to 200 bp, for example, 15 to 40 bp, 150 to 180 bp, and the like.

In certain specific embodiments, the nucleic acid molecule is capable of encoding a proteinic enzyme having epoxy group-removing catalytic activity.

Plants in the invention are not particularly limited, and may be food crops, economic crops, medicinal plants, and the like, or may be herb plants or woody plants. Examples of food crops include, but are not limited to, for example, rice, *Triticum aestivum, Hordeum vulgare, Oryza sativa, Hordeum vulgare* var. *coeleste, Setaria italica* var. *germanica, Glycine max*, and the like. Examples of woody plants comprise fruit trees, such as evergreen woody fruit trees or Rosaceae fruit trees. Examples of plants further comprise *Medicago sativa, Thinopyrum* sp., *Lolium perenne, Purus frumentum, Pennisetum sinese* Roxb, *Pennisetum purpureum, Hordeum vulgare, Arachis hypogaea, Gossypium* sp., and the like. The plants of the invention may also be hybrid plants, for example, plants obtained by crossing the above-mentioned plants.

In certain specific embodiments, the disease comprises a plant disease caused by a fungi of *Fusarium, Cephalosporium, Myrothecium* or *Trichoderma*. Such plant disease may, for example, be root rot, stem rot, stem base rot, flower rot and ear rot.

A second aspect of the invention provides a plant cell comprising an exogenous nucleic acid molecule having a sequence selected from the group consisting of (a) to (e) introduced by means of genetic engineering.

A third aspect of the invention provides a transgenic plant obtained by introducing an exogenous nucleic acid into a host plant by means of genetic engineering.

A fourth aspect of the invention provides use of a polypeptide having epoxy group-removing catalytic activity for detoxification of vomitoxin, wherein the active polypeptide has an amino acid sequence as set forth in SEQ ID NO: 36.

In certain specific embodiments, the polypeptide is capable of catalyzing the reaction between an epoxy group in vomitoxin and glutathione to produce a glutathionylated derivative.

In certain specific embodiments, the use refers to detoxification of a sample contaminated with vomitoxin. Preferably, the sample is a food, a feed or a beverage.

In certain specific embodiments, the sample further comprises glutathione, or glutathione is added to the sample.

In certain specific embodiments, the sample is derived from a plant infected with a fungi of *Fusarium, Cephalosporium, Myrothecium* and/or *Trichoderma*.

In certain specific embodiments, the fungi of Fusarium is selected from *Fusarium graminearum, Fusarium oxysporum, Fusarium moniliforme, Fusarium sporotrichioides, Fusarium roseum, Fusarium culmorum* and *Fusarium nivale*.

In certain specific embodiments, it is the use in the field of food or feed processing.

A fifth aspect of the invention provides a method for reducing or alleviating cytotoxicity, comprising introducing a polypeptide having an amino acid sequence as set forth in SEQ ID NO: 36 into a cell or contacting the polypeptide with a cell.

In certain specific embodiments, the method further comprises introducing a gene encoding the polypeptide into the cell. The nucleic acid molecule of the invention is capable of encoding a de-epoxidation proteinic enzyme, so that the transgenic plant has the ability to remove epoxy groups for trichothecenes, thereby reducing the amount of such toxins in the plant. Examples of such toxins include, but are not limited to, deoxynivalenol (DON), 15-acetyl-deoxynivalenol (15-ADON), 3-acetyl-deoxynivalenol (3-ADON), nivalenol (NIV), fusarenon-X (Fus-X), diacetoxyscirpenol (DAS), T-2 toxin (T-2), and HT-2 toxin (HT-2).

BRIEF DESCRIPTION OF THE DRAWINGS

FIG. 3A represents the quantitative result of DON-GSH; panel FIG. 3B represents the quantitative result of DON; panel FIG. 3C represents the quantitative result of 3-ADON-GSH; and panel FIG. 3D represents the quantitative result of 3-ADON.

FIG. 4A shows the disease situations on the 21$^{st}$ day of inoculation (in the figure, A represents the transgenic positive plant, and B represents the receptor material for transgenesis); panel FIG. 4B shows the statistical data of the number of diseased spikelets in three transgenic lines with overexpression of ThFhb7; and panel FIG. 4C shows the statistical data of the number of diseased spikelets in three transgenic lines with original expression of ThFhb7.

FIGS. 5A-5C show the results of broad resistance of ThFhb7 transgenic lines to *Fusarium* sp. Panel FIG. 5A represents the result of resistance of ThFhb7 transgenic lines to *F. graminearum*; panel FIG. 5B represents the result of resistance of ThFhb7 transgenic lines to *F. asiaticum*; and panel FIG. 5C represents the result of resistance of ThFhb7 transgenic lines to *F. pseudograminearum*.

FIGS. 6A and 6B show the experimental results of resistance to wheat stem base rot conferred by ThFhb7. Panel FIG. 6A represents the effect of ThFhb7 on the disease situations of wheat stem base rot; and panel FIG. 6B represents the statistical results of the death rate of ThFhb7 transgenic plants in the stem base rot resistance experiment.

FIG. 7 shows the identification result of resistance of ThFhb7 transgenic maize to Fusarium head blight.

FIG. 13 shows a graph of SDS-PAGE analysis after purification of an active polypeptide.

FIGS. 14A and 14B show the effect of the amount of active polypeptide on the enzymatic reaction. Panel FIG. 14A shows the reduction of the enzymatic reaction substrate, vomitoxin (DON); and panel FIG. 14B shows the production of the enzymatic reaction product, DON-GSH.

FIGS. 15A and 15B show the effect of pH of the reaction buffer on the enzymatic reaction. Panel FIG. 15A shows the reduction of the enzymatic reaction substrate, vomitoxin (DON); and panel FIG. 15B shows the production of the enzymatic reaction product, DON-GSH.

FIG. 16A shows the reduction of the enzymatic reaction substrate, vomitoxin; and panel FIG. 16B shows the production of the enzymatic reaction product, DON-GSH.

DETAILED DESCRIPTION OF EMBODIMENTS

Figure 1:
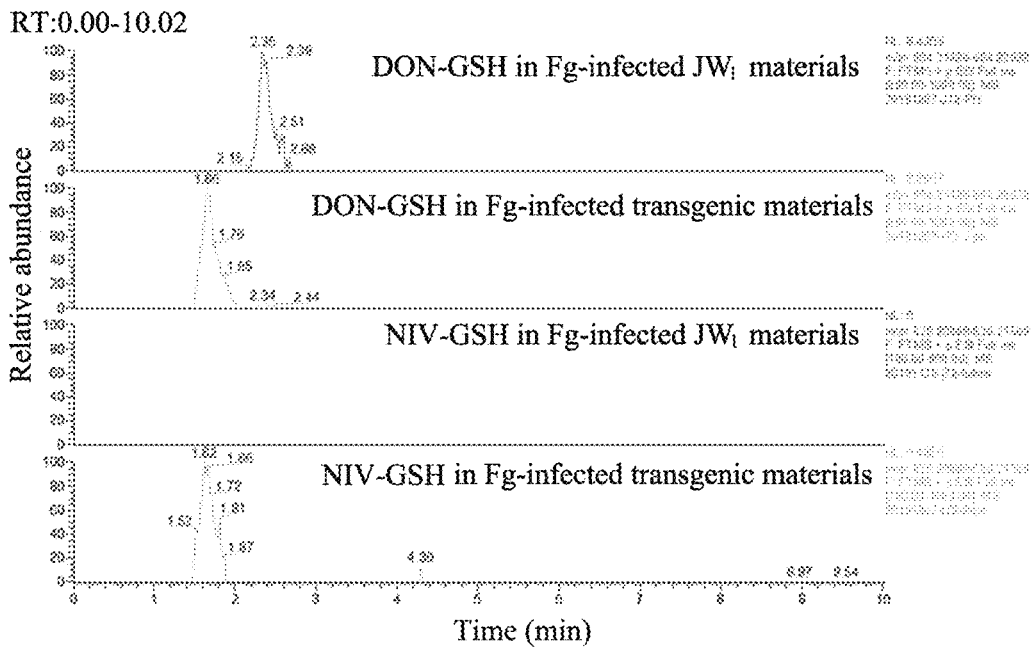
FIG. 1 shows extracted ion chromatograms of *F. graminearum* (F.g)-infected transgenic wheat by LC-HRMS in full scan mode.

Various exemplary implementations of the present invention are now described in detail. The detailed description should not be considered as a limitation on the present invention but should be understood as a more detailed description of certain aspects, characteristics, and embodiments of the present invention.

It should be understood that the terms described in the present invention are only used to describe specific implementations rather than to limit the present invention. In addition, for the numerical ranges in the present invention, it should be understood that the upper limit and the lower limit of the range and each intermediate value between them are specifically disclosed. Each smaller range between an intermediate value among any stated values or within any stated range and an intermediate value among any other stated values or within any other stated range is also encompassed in the present invention. The upper and lower limits of these smaller ranges can be independently included or excluded from the range.

Unless otherwise specified, all technical and scientific terms used herein have the same meaning as commonly understood by those of ordinary skill in the art to which the present invention belongs. Although the present invention only describes preferred methods and materials, any methods and materials similar or equivalent to those described herein can also be used in the implementation or testing of the present invention. All documents mentioned in this specification are incorporated by reference to disclose and describe methods and/or materials related to the documents. In the event of conflict with any incorporated document, the content of this specification shall prevail. "%" is a percentage based on weight, unless otherwise specified.

Herein, for the term "base at position y" or similar expressions, the sequence of the de-epoxidase gene derived from *Thinopyrum ponticum* is taken as a position reference, that is, the nucleic acid sequence as set forth in SEQ ID NO: 1 is used as a position reference unless explicitly specified otherwise.

Herein, the term "active polypeptide" refers to a polypeptide having catalytic activity of de-epoxidase, i.e., an active polypeptide that converts an epoxy group into another group or removes the epoxy group. It is also sometimes referred to herein as a "proteinic enzyme".

Herein, the term "epoxy group-removing catalytic activity" refers to an activity or function of removing an epoxy group (preferably the epoxy group formed between the 12-position carbon and the 13-position carbon) in vomitoxin. The specific catalytic process is as follows:

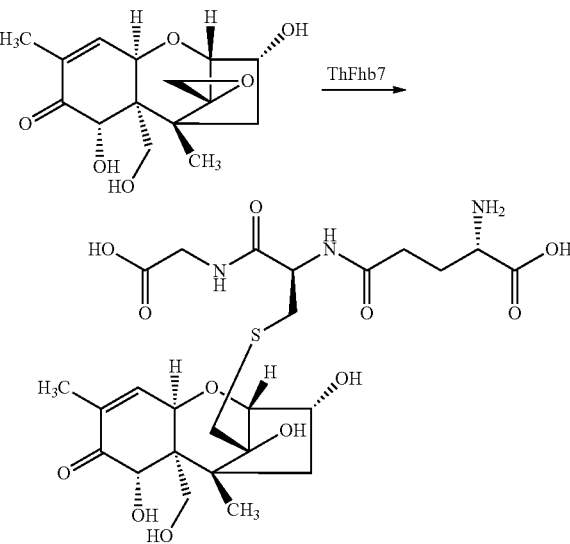

Example 1

I. Experiment on Resistance of Transgenic Wheat to *Fusarium* Head Blight

1. Construction of an Overexpression Vector

The CDS region (847 bp) of the ThFhb7 gene of *Thinopyrum* was amplified using the genomic DNA of *Thinopyrum ponticum* as a template, with the primer sequences designed as follows:

(SEQ ID NO: 37)

Forward primer:

5'-TGCAGCCCGGGGATCCAGAAATCCACCCATCGTCATCACC-3';

(SEQ ID NO: 38)

reverse primer:

5'-ACCTGTAATTCACACGTGCTACTTCACCTCGGCATACTTGTC-3'.

The underlined portions are extended sequences complementary to the end of the linearized vector. The whole gene sequence of ThFhb7 cDNA was obtained by PCR. After the vector pCAMBIA3300 was treated with endonuclease BamHI, the PCR product and the linearized plasmid were purified and recovered, the PCR product was inserted into the MCS downstream of the strong promoter of pCAMBIA3300 using the In-Fusion HD cloning kit and transformed into *Escherichia coli* DH5a. After identification by colony PCR, the positive monoclonal bacterial solution was sequenced for verification, and the sequence was set forth in SEQ ID NO: 1. The correct plasmid after sequence verification was sent to the wheat transformation platform of the National Key Laboratory of Shandong Agricultural University for transgenesis in wheat, and the receptor was the wheat variety fielder.

2. Construction of an Original-Expression Vector

The promoter region (1308 bp) and the CDS region (847 bp) of the *Fusarium* head blight-resistant ThFhb7 gene of *Thinopyrum* were amplified using the genomic DNA of *Thinopyrum ponticum* as a template, with the primer sequences designed as follows:

(SEQ ID NO: 39)

Forward primer:

5'-ACATGATTACGAATTCTTCTACTAGTGCCCCACCtACG-3';

(SEQ ID NO: 40)

Reverse primer:

5'-ACCTGTAATTCACACGTGCGACCAGCCAGGAAACACCACTG-3'.

The underlined portions are extended sequences complementary to the end of the linearized vector. The sequence comprising the ThFhb7 promoter and the open reading frame was obtained by PCR. After the vector pCAMBIA3300 was treated with endonuclease EcoRI, the PCR product and the linearized plasmid were purified and recovered, and the fragment was inserted into the pCAMBIA3300 vector with the ubi promoter removed using the In-Fusion HD cloning kit and transformed into *Escherichia coli* DH5a. After identification by colony PCR, the positive monoclonal bacterial solution was sequenced for verification. The correct plasmid after sequence verification was sent to the wheat transformation platform of the National Key Laboratory of Shandong Agricultural University for transgenesis in wheat, and the receptor was the wheat variety Kenong 199 (KN199).

3. PCR Detection of ThFhb7 Transgenic Plants

The young leaves of transgenic plants were taken, and the genomic DNA of wheat was extracted by CTAB method. Using the sequence of pCAMBIA3300 expression vector and the sequence information of ThFhb7 promoter region and CDS region, primers for spanning the overexpression and original-expression vectors were developed respectively, and PCR was performed on transgenic plants. Amplification products were detected by 1% agarose gel electrophoresis. The primers for spanning the overexpression vector were F: 5'-TGCAGTCCCTCCGAAACATG-3' (SEQ ID NO: 41); R: 5'-CAAATGGACGAACGGATAAACC-3' (SEQ ID NO: 42). The primers for spanning the original-expression vector were F: 5'-AGCGGAAACACG-CATCTGACCT-3' (SEQ ID NO: 43); R: 5'-TTACCCGC-CAATATATCCTGTC-3' (SEQ ID NO: 44).

4. RT-PCR Detection of ThFhb7 Transgenic Plants

The leaves of wheat seedlings were ground into powder in liquid nitrogen and extracted using TRIzol® Reagent according to the instructions. Genomic DNAs were removed and RNAs were reversely transcribed into cDNAs using a reverse transcription kit. The fluorescent quantitative primers F: 5'-TGATTCTTCTTCCGTTTCTAAGGA-3' (SEQ ID NO: 45); R: 5'-ATGTCAAAGGAGTCGCCGACGA-3' (SEQ ID NO: 46) were designed according to the ThFhb7 gene sequence. RT-PCR analysis was performed using a Roche LightCycler 480. The housekeeping gene β-actin was used as an internal standard. The relative expression level of ThFhb7 was calculated by CT value, the wheat transgenic lines with high expression were selected, $T_3$ plants were obtained by strict bagging and consecutive selfing, and phenotype identification of resistance to *Fusarium* head blight was further carried out.

5. Phenotype Identification of Resistance of ThFhb7 Transgenic Plants to Fusarium Head Blight The strain of *F. graminearum* was taken out, and after inoculation and activation, the activated mycelia were picked, inoculated into CMC sporulation media, and cultured and induced to produce conidia. The mycelia were filtered off with gauzes, and the culture solution was collected into a sterile Erlenmeyer flask; the supernatant was discarded by centrifugation, an appropriate amount of ddH$_2$O was added, and the spore concentration was adjusted to $2 \times 10^5$ spores/mL for inoculation on individual flowers; the solution was aliquoted into centrifuge tubes and stored at −20° C. for later use. In the early flowering stage of wheat, 10 μl of spore suspension was pipetted with a pipette and injected between the lemma and palea of the middle-upper florets of a spikelet; plastic bags were put on, and the plastic bags were removed after moisturizing for 72 h. About 30 ears were inoculated for each transgenic line, and one spikelet was inoculated for each individual plant. 21 days after inoculation, the number of diseased spikelets (NDS) was counted.

6. Activation of Culture of *F. graminearum*

The mycelia on a potato culture medium were scraped with a toothpick and put into a mung bean culture medium, and the culture was shaken at 28° C. and 200 rpm for 3 days; after the shaking culture was completed, the culture solution was filtered with a filter cloth, aliquoted into 50 ml centrifuge tubes and centrifuged, the supernatant was discarded, and 30 ml of sterilized water was added, vibrated and mixed well; centrifugation was performed at 4,000 rpm for 20 min, and the supernatant was discarded; the precipitate was resuspended with a small amount of sterilized water, detected for the spore amount under a microscope and diluted to a concentration of $1 \times 10^5$ spores/ml based on the spore amount.

7. Inoculation of Conidia on Wheat Materials by a Dripping Method for Individual Flowers At the flowering stage of wheat, two spikelets at the base of a floret at the same ear position (usually the two basal florets on the left and right of the third spikelet from the top of the ear) were inoculated with 10 μL of conidia of *F. graminearum* (at a concentration of 1×10⁵ spores/ml). The inoculation site was marked and bagged for moisturizing. During the whole inoculation process, try not to expose the spikelets directly to the air to avoid drying. 72 h after the inoculation, the inoculated ears were sampled, and the collected samples were quickly frozen with liquid nitrogen and transferred to an ultra-low temperature refrigerator at −80° C. and stored for later use.

8. Extraction of Toxin Derivatives

After wheat samples were ground, 1.5 ml of pre-cooled 75% methanol aqueous solution (comprising 0.1% formic acid) was added. The mixture was vibrated for 10 s, sonicated for 30 min at room temperature, and the supernatant was taken and transferred to a new centrifuge tube. The supernatant was concentrated in vacuo to a dry powder. Before injection, the dry powder was resuspended with 100 μL of 20% acetonitrile solution, filtered through a 0.22 μm filter membrane, and transferred to an injection vial for LC-HRMS detection.

9. Experimental Results

In order to identify the in vivo biochemical and biological roles of ThFhb7 in wheat, firstly, this gene driven by the maize ubiquitin promoter was overexpressed in wheat, and the ears of $T_3$-generation homozygous transgenic wheat were inoculated with *F. graminearum*. At the flowering stage of wheat, samples were taken for detection 72 hours after inoculation with *F. graminearum*. The detection results were shown in FIG. 1. In positive ion mode by LC-HRMS (Full scan), DON-GSH adduct was detected in Fg-infected ThFhb7 transgenic wheat, with an m/z of 604.21730 (corresponding to [M+H]⁺, Δ±5 ppm); and NIV-GSH adduct was detected in Fg-infected ThFhb7 transgenic wheat, with an m/z of 620.21199 (corresponding to [M+H]⁺, Δ±5 ppm). However, no corresponding GSH adduct was detected in the corresponding control (*F. graminearum*-infected wheat receptor material for transgenesis).

Figure 2:
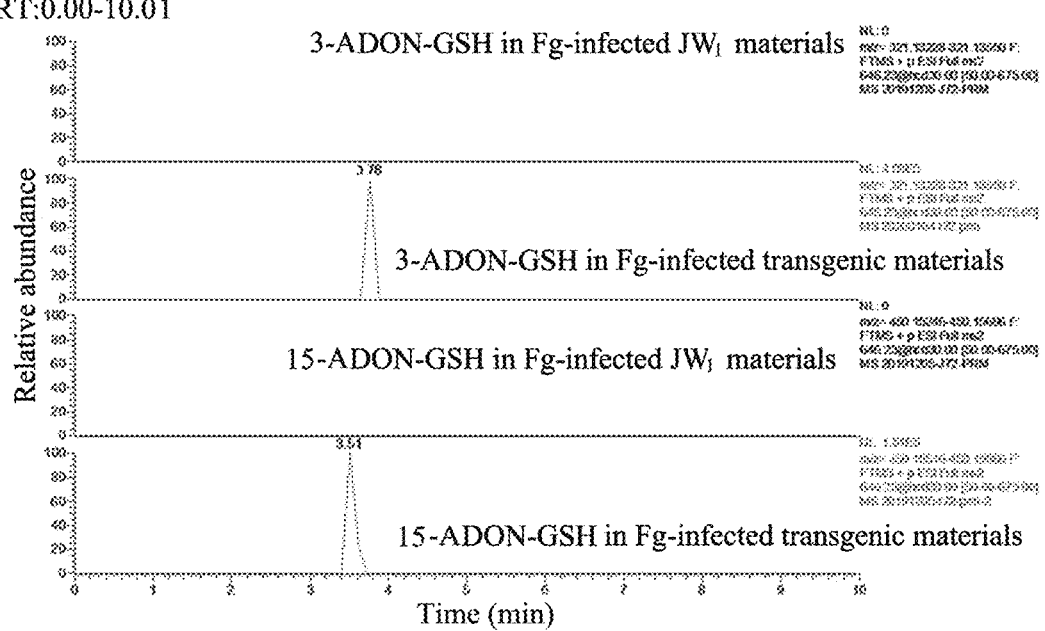
FIG. 2 shows extracted ion chromatograms of F.g-infected transgenic wheat by LC-HRMS (/MS) in PRM mode.

Since 3-ADON and 15-ADON were isomers with the same molecular weight, and the first-order spectrum in Full scan mode cannot distinguish them, the positive ion PRM mode of LC-HRMS (/MS) was used for detection. The detection results were shown in FIG. 2. 3-ADON-GSH adduct was detected in Fg-infected ThFhb7 transgenic wheat with precursor ion m/z of 646.22764 (corresponding to [M+H]⁺, Δ±5 ppm) and product ion m/z of 321.11210; and 15-ADON-GSH adduct was detected in Fg-infected ThFhb7 transgenic wheat with precursor ion m/z of 646.22764 (corresponding to [M+H]⁺, Δ+5 ppm) and product ion m/z of 450.15471. However, no corresponding GSH adduct was detected in the corresponding control wheat receptor fielder for transgenesis.

Conclusion: Trichothecene mycotoxins were produced within 72 hours when a single *F. graminearum* species infected wheat ears at the flowering stage. In this experiment, DON, 3-ADON, 15-ADON and a small amount of NIV were clearly detected by LC-HRMS, but other toxins such as T2, HT-2, and the like were not detected due to the extremely low level. The experimental results showed that when *F. graminearum* infected transgenic wheat overexpressing ThFhb7, DON, 3-ADON, 15-ADON and NIV can be efficiently catalyzed into glutathione adducts. ThFhb7 transgenic wheat had improved ability of toxin tolerance, demonstrating that ThFhb7 can take a trichothecene mycotoxin as a substrate and catalyze it into a corresponding GSH adduct, and can improve the resistance of wheat to Fusarium head blight.

II. Quantitative Detection of Toxins and their Derivatives in Transgenic Wheat In view of the above experiments, it was proved that ThFhb7 can catalyze DON, 3ADON, 15ADON, NIV and other toxins into derivatives in the form with GSH in wheat when the wheat was infected by *F. graminearum*. In order to further confirm the amount changes of these toxins, these toxins were further quantified by Liquid Chromatography High-Resolution Mass Spectrometry, LC-HRMS (/MS) in PRM mode. Due to the higher requirement of the toxin amount in PRM mode, in this experiment, only relevant quantitative detection of DON and 3ADON in transgenic wheat overexpressing ThFhb7 was carried out. The specific results were shown in FIGS. 3A-3D.

Figures 3A, 3B, 3C, 3D, 4A, 4B, 4C:
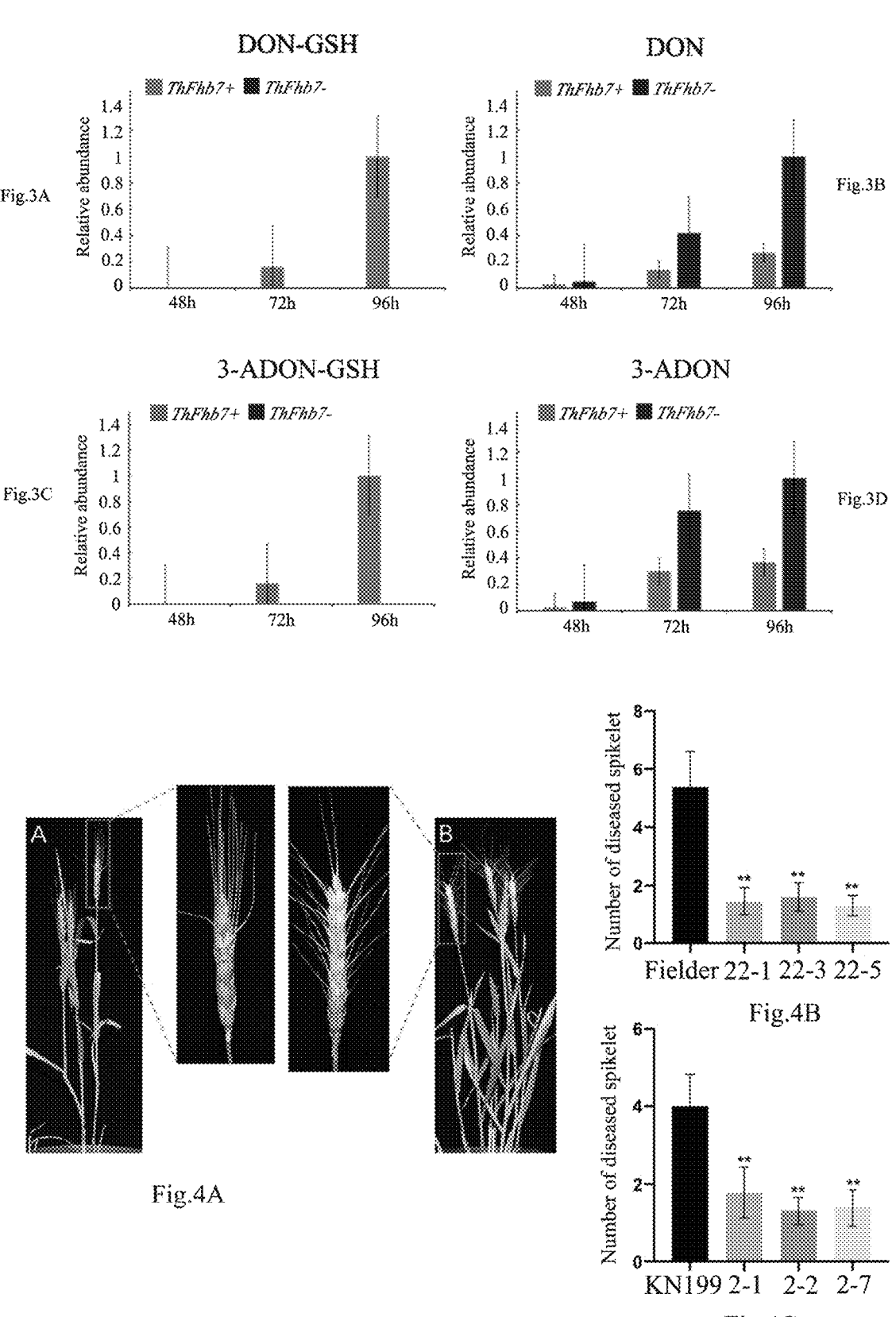
FIGS. 3A-3D show quantitative detection results of toxins and their derivatives by LC-HRMS (/MS) in PRM mode. Panel
FIGS. 4A-4C show experimental results of identification of the phenotype of resistance to Fusarium head blight in transgenic plants. Panel

After ears of ThFhb7 transgenic wheat were inoculated with *F. graminearum*, the samples were collected at different time points, and then the amounts of DON, DON-GSH, 3-ADON and 3-DON-GSH were determined. FIG. 3A shows that in the transgenic wheat comprising ThFhb7, DON-GSH was formed through specific catalysis, while the accumulation of DON-GSH cannot be detected in the control material $JW_1$ without ThFhb7. The results of FIG. 3B showed that after inoculation with Fg, the substrate DON was significantly reduced (about ⅓) as compared with the wheat without ThFhb7, as DON-GSH was abundantly synthesized in the presence of ThFhb7. Similarly, in FIG. 3C, 3-ADON-GSH can be synthesized in the transgenic wheat comprising ThFhb7, while 3-ADON-GSH (green) cannot be detected in the control material $JW_1$ without ThFhb7. In FIG. 3D, after the ears were inoculated with Fg, 3-ADON was significantly reduced (about ⅓) in the wheat comprising ThFhb7 as compared with the control receptor material without ThFhb7. This experiment proved that ThFhb7 can efficiently derivatize DON and 3-ADON into DON-GSH after the wheat was infected by *F. graminearum*, thereby reducing the in vivo accumulation of DON toxins in wheat and playing a role in detoxification.

The results of quantitative detection of toxins and their derivatives showed that a large amount of DON and 3-ADON were produced when wheat was infected by *F. graminearum*. The quantitative results of PRM showed that when F.g infected the transgenic wheat comprising *Fusarium* head blight-resistant ThFhb7 gene, the amounts of DON and 3-ADON decreased by about ⅔ as compared with the control, and accordingly DON-GSH and 3-ADON-GSH increased with the decrease of DON and 3-ADON. ThFhb7 transgenic wheat had improved ability of toxin tolerance, demonstrating that ThFhb7 can take DON and 3-ADON as substrates to catalyze them into the corresponding GSH adducts, and can play a role in detoxification in vivo.

III. Phenotype of Resistance to *Fusarium* Head Blight in Transgenic Wheat and Statistical Data On the basis of toxin analysis of transgenic wheat infected by *F. graminearum*, the disease resistance of transgenic wheat was investigated. The overexpression type transgenic line forced to express the transgene under the ubiquitin promoter with the receptor material being the wheat variety fielder, and the original-expression type transgenic line produced by transforming the wheat variety KN199 using the original promoter of ThFhb7 donor material were included, and the related disease resistance was investigated.

A spore suspension of *F. graminearum* was prepared according to the above method, the concentration was adjusted to $2 \times 10^5$ spores/mL, and 10 μl of spore suspension was inoculated on the middle-upper portions of an ear, while the ear was bagged for moisturizing. When spores germinated on the spikelet and mycelia were clearly visible, the bag was removed. About 30 ears were inoculated for each line, the disease situation was observed, the number of diseased spikelets 21 days after inoculation was counted, and difference analysis was performed. The results were shown in FIGS. 4A-4C. It was found that the number of diseased spikelets of the overexpression type and original-expression type transgenic lines was significantly less than that of the control receptor material.

Conclusion: After overexpression vector and the original-expression vector for ThFhb7 gene were constructed, the two vectors were introduced into the corresponding wheat receptors to obtain $T_0$ plants. Through PCR and RT-PCR screening, the wheat lines with high ThFhb7 expression were strictly self-pollinated until $T_3$. The positive transgenic lines were identified for resistance to Fusarium head blight in the ear by the dripping method for individual flowers, and the number of diseased spikelets of the overexpression type and original-expression type transgenic lines was significantly less than that of the control receptor material. The above experimental results showed that the expression of ThFhb7 can significantly improve the resistance to Fusarium head blight in wheat.

Example 2

This example is an experiment of resistance of transgenic wheat to a variety of species of *Fusarium* and to stem base rot.

1. Experimental Materials

The plant material, KN199, transgenic lines with original expression of ThFhb7, and strain materials comprising dominant strains of *Fusarium* head blight in wheat, *F. graminearum* (or F.g) and *F. asiaticum*, and dominant strains of wheat stem base rot, *F. pseudograminearum*, were all preserved in our laboratory.

2. Experimental Methods

The *Fusarium* strains were activated by a method similar to that described above and stored for later use. The selected full seeds of a receptor material for transgenesis, KN199, and of the transgenic line were cultured to the two-leaf-and-one-leaflet stage to three-leaf-and-one-leaflet stage, and the leaf sites with flat surfaces and the same width were selected and divided into leaf segments of 3 to 3.5 cm. The fracture of the leaf segment needed to be neat and did not cause damage to mesophyll tissues. A circular wound was made in the middle of the upper surface of the leaf segment, and the circular wound site was inoculated with 1 to 2.5 μL of suspensions of different *Fusarium* spores at a concentration of $2 \times 10^5$ spores/mL. 24 replicates were made for each strain and cultured at 25° C. under humid conditions for 3 days, and the spread of the disease spots was observed.

The JM22 and RJM22 seedlings with the same growth situation were selected and cultured to the four-leaf-and-one-leaflet stage. A regular circular wound was made with a pipette tip at the stem base, the wound site was inoculated with 2.5 μL conidia suspension of *F. pseudograminearum* and moisturized at 28° C. for disease development for 15 days, the disease situation of the plants was observed, and the death rate was calculated.

3. Experimental Results

3.1 Identification of Resistance to Multiple Strains in Ex-Vivo Leaves

Broad resistance of Fhb transgenic lines to *Fusarium* sp. was identified using ex-vivo leaves. Seedlings were cultured to the two-leaf-and-one-leaflet stage to three-leaf-and-one-leaflet stage, the leaves at the same leaf position were selected, and divided into leaf segments of 3 to 3.5 cm. The fracture of the leaf segment needed to be neat and did not cause damage to mesophyll tissues. A circular wound was made with a pipette tip in the middle of the upper surface of the leaf segment, and the circular wound site was inoculated with 2.5 μL of suspensions of different *Fusarium* spores at a concentration of $2 \times 10^5$ spores/mL. 24 replicates were made for each strain and cultured at 25° C. under humid conditions for 3 days, and the spread of the disease spots was observed. *F. graminearum* and *F. asiaticum* were the two main strains causing Fusarium head blight. *F. pseudograminearum* was the main strain causing wheat stem base rot. First, a circular wound was made with a pipette tip in the center of an ex-vivo leaf of a seedling with two leaves and one leaflet, and the wound site was inoculated with 2 μL of *Fusarium* conidia suspension and moisturized for disease development at 25° C. for 3 days. The area of necrotic spots was then measured for assessment of resistance to *Fusarium* sp. The results were shown in FIG. 5A, FIG. 5B and FIG. 5C. Compared with the disease-susceptible control, KN199, all the ThFhb7 transgenic plants had significantly reduced diseased spot area on leaves when the plants were inoculated with spore suspensions of *F. graminearum, F. asiaticum* and *F. pseudograminearum*.

3.2 Results of Resistance to Stem Base Rot

Using the method of wound inoculation at the stem base, the receptor material and the ThFhb7 transgenic material were inoculated with conidia suspensions of *F. pseudograminearum* for 15 days, and the results were shown in FIG. 6A. The results showed that the degree of disease at the stem base of transgenic wheat was less severe than that of the control. The results of FIGS. 6A and 6B showed that the death rate of ThFhb7 transgenic plants was significantly lower than that of the wild type. In addition, *F. pseudograminearum* was the dominant strain causing wheat stem base rot. In FIG. 6A, a circular wound was made with a pipette tip at the stem base of a wheat seedling with four leaves and one leaflet, the wound site was inoculated with 2 μL of *Fusarium* conidia suspension and moisturized for disease development at 25° C. for 15 days, and the disease situations of stem base rot were observed. FIG. 6B shows the statistical data of death rates and difference analysis after 15 days of disease development at 25° C.

Conclusion: Broad resistance of ThFhb7 transgenic lines to *Fusarium* sp. was identified using ex-vivo leaves of ThFhb7 transgenic lines and the receptor material, KN199. The results showed that the disease spot areas of *F. graminearum, F. asiaticum* and *F. pseudograminearum* on leaves were significantly smaller than that of the disease-susceptible control, indicating that ThFhb7 had a relatively broad-spectrum resistance to *Fusarium* sp.; wherein *F. pseudograminearum* was the dominant strain causing wheat stem base rot. In addition, in the experiment, the short fragment translocation line material R-JM22 comprising ThFhb7 with JM22 as the background, and the ThFhb7 transgenic line were inoculated with *F. pseudograminearum* to identify the resistance of these two materials to wheat steam base rot. The results were consistent with the leaf phenotypes, and both materials showed good resistance to wheat stem base rot, indicating that ThFhb7 can improve the resistance of wheat to stem base rot.

Example 3

This example is a preliminary resistance experiment of the T$_0$-generation plants of transgenic maize.

1. Experimental Materials

*Thinopyrum ponticum* was used to amplify the target gene ThFhb7 sequence fragment, and the overexpression vector was used to transform the receptor material, KN5585. The expression vector pCAMBIA3300 was provided by the Chinese Academy of Agricultural Sciences, and the *Escherichia coli* DH5α strain was preserved in the laboratory.

2. Experimental Methods

Using a method similar to Example 1, transgenesis in maize was carried out by the National Key Laboratory of Shandong Agricultural University. Furthermore, PCR detection and RT-PCR detection of ThFhb7 transgenic maize plants and phenotype identification of plant resistance to Fusarium head blight were carried out using the above-mentioned methods.

The positive transgenic seedlings of ThFhb7 transgenic T$_3$ plants were selected and cultured to the two-leaf-and-one-leaflet stage, and the leaf sites with flat surfaces and the same width were selected and divided into leaf segments of 3 to 3.5 cm. The fracture of the leaf segment needed to be neat and did not cause damage to mesophyll tissues. A circular wound was made in the middle of the upper surface of the leaf segment, and the circular wound was inoculated with 1 to 2.5 μL of the spore suspension of *F. graminearum* at a concentration of 2×10$^5$ spores/mL. 10 replicates were made for each mutant and cultured at 25° C. under humid conditions for 3 days, and the spread of the disease spots was observed.

3. Experimental Results 3.1 Identification of Resistance of ThFhb7 Transgenic Plants to Fusarium Head Blight The resistance of ThFhb7 transgenic maize plants to *Fusarium* head blight was identified using ex-vivo leaf phenotypes of three T$_3$ transgenic positive lines (W1, W2, W3). A circular wound was made in the center of an ex-vivo leaf, and the wound was inoculated with a spore suspension of *F. graminearum*; and after culturing for 3 days under humid conditions, the size of disease spots was measured and the difference compared with the control was analyzed.

Three T$_3$ transgenic lines with high expression were selected for assessment of resistance to Fusarium head blight using ex-vivo leaves, and the disease spot area was significantly reduced as compared with the receptor material as a disease-susceptible control. The area of necrotic spots was calculated 3 days after inoculation, and at least 10 ex-vivo leaves were used in the detection of each sample. The experimental results were shown in FIG. 7. The experimental results showed that by constructing an overexpression vector of ThFhb7 gene and transferring it into maize to obtain T$_0$ plants, and screening by PCR and RT-PCR, the disease resistance of the maize lines with high ThFhb7 expression was identified using ex-vivo leaves, and the positive transgenic lines were identified for the resistance to Fusarium head blight, showing that the disease spot area of the ex-vivo leaves of transgenic maize was significantly smaller than that of the disease-susceptible control. This experiment preliminarily showed that the expression of ThFhb7 can also significantly improve the resistance of maize to *F. graminearum* infection.

Example 4

This example is for the study of mutation of the nucleic acid molecule and function of mutants.

1. Experimental Materials

Jimai 22 (JM22) was used as the background and hybridized with a wheat material having ThFhb7 introduced, thereby obtaining wheat materials numbered A052-2 and A079-3, which were created and preserved by our laboratory in the early stage.

2. Construction of Mutant Populations

In the early time at the laboratory, according to the results of the EMS pretreatment experiment, seeds were treated with 0.8% EMS solution in the dark, shaken at 150 rpm for 10 h at 25° C., and then continuously rinsed with tap water for 3 to 4 h. 2,500 seeds were treated each time, and a total of 10,000 seeds were treated in 4 batches, all of which were planted in the field. M1 plants were strictly bagged and selfed, and one seed was taken from each plant after maturity to form M2 single-seed descent population. Each of M2 individual plants was numbered and the leaves were taken for subsequent DNA extraction, and the plants were harvested as individual plants after maturity.

3. TILLING Detection 3.1 PCR Amplification

Since the full-length of the gene is 864 bp, we sequenced the full-length of the gene using the traditional Sanger sequencing platform and screened for mutants. Full-length sequencing primers for ThFhb7

```
                                        (SEQ ID NO: 47)
F:
5'-TTCATCATCCTGCTAGGCGATAAGA-3';

(SEQ ID NO: 48)
R:
5'-CTACTTCACCTCGGGGCATACTTGTC-3'.
```

We utilized UNG enzymatic treatment in combination with targeted preamplification using dUTPs, and deoxythymidine triphosphates (dTTPs) were replaced with deoxyuridine triphosphates (dUTPs) in PCR. Uracil DNA N-glycosylase (UNG) was used to degrade any uracil-containing PCR product, i.e., eliminate residual contaminants, prior to initiating PCR. PCR amplification was performed in 10 μl total volume of reactions, comprising 1× Multiplex PCR Mastermix (UNG) (CWBIO Bio, China), 0.7 µM of each primer and 100 ng of template DNAs. Amplification curves comprised 1 cycle at 50° C. for 2-8 min and 1 cycle at 95° C. for 5 min; followed by 35 cycles performed at 94° C. for 30 s, at 60° C. for 30 s and 72° C. for 50 s; and a final extension at 72° C. for 10 min. The homozygous and heterozygous states for each point mutation were verified by manual inspection of the signal peak map by DNAMAN. Homozygous mutants were screened for further phenotype identification of FHB resistance.

3.2 Phenotype Identification of Resistance to *Fusarium* Head Blight

The selected homozygous mutant plants were cultured to the two-leaf-and-one-leaflet stage to three-leaf-and-one-leaflet stage, and the leaf sites with flat surfaces and the same width were selected and divided into leaf segments of 3 to 3.5 cm. The fracture of the leaf segment needed to be neat and did not cause damage to mesophyll tissues. A circular wound was made in the middle of the upper surface of the leaf segment, and the circular wound site was inoculated with 1 to 2.5 µL of a spore suspension of *F. graminearum* at a concentration of $2\times10^5$ spores/mL. 10 replicates were made for each mutant and cultured at 25° C. under humid conditions for 3 days, and the spread of the disease spots was observed.

4. Experimental Results 4.1 Mutant Screening

Figure 8:
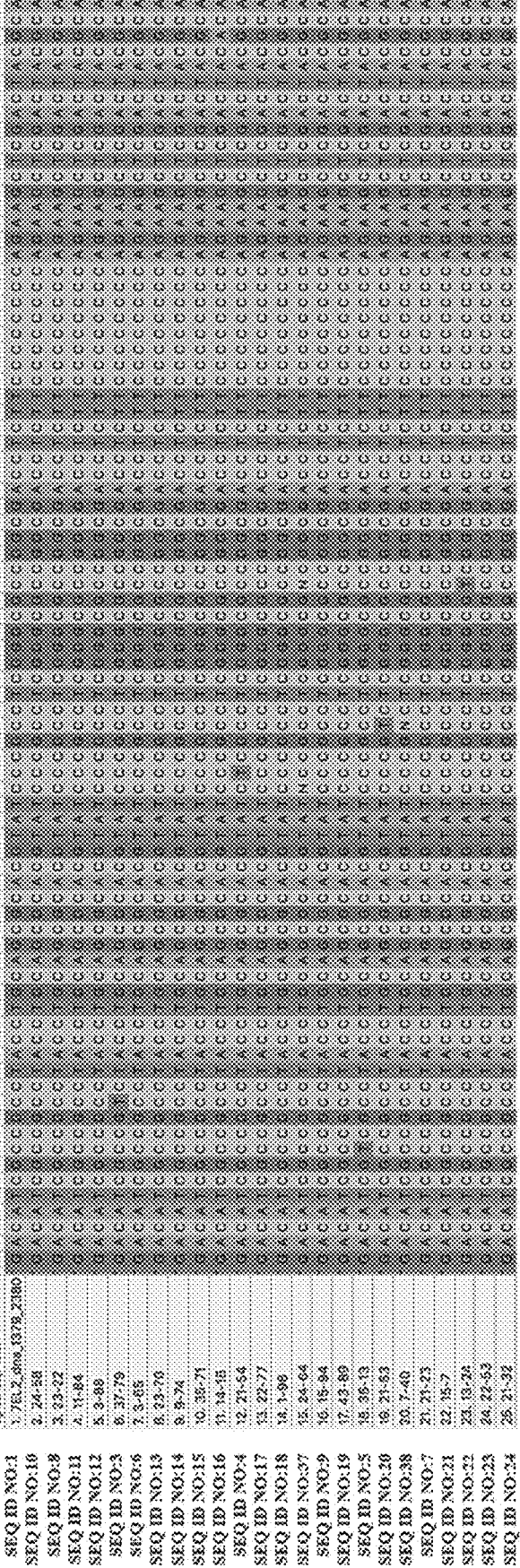
FIG. 8 shows the alignment result of partial mutant sequences of ThFhb7.

About 4000 M2 mutants were screened by direct sequencing (Sanger) of the full-length PCR product of ThFhb7 (primers were the same as above). To avoid possible template contamination during PCR, deoxyuridine triphosphates (dUTPs) were used instead of deoxythymidine triphosphates (dTTPs) in PCR, and uracil DNA N-glycosylase (UNG) treatment was performed to degrade any uracil-containing PCR products in the template. Finally, 24 mutants with amino acid changes were obtained by screening, and the alignment results of partial mutant sequences were shown in FIG. 8.

4.2 Phenotype Identification of Resistance of Mutants to Fusarium Head Blight

Figure 9:
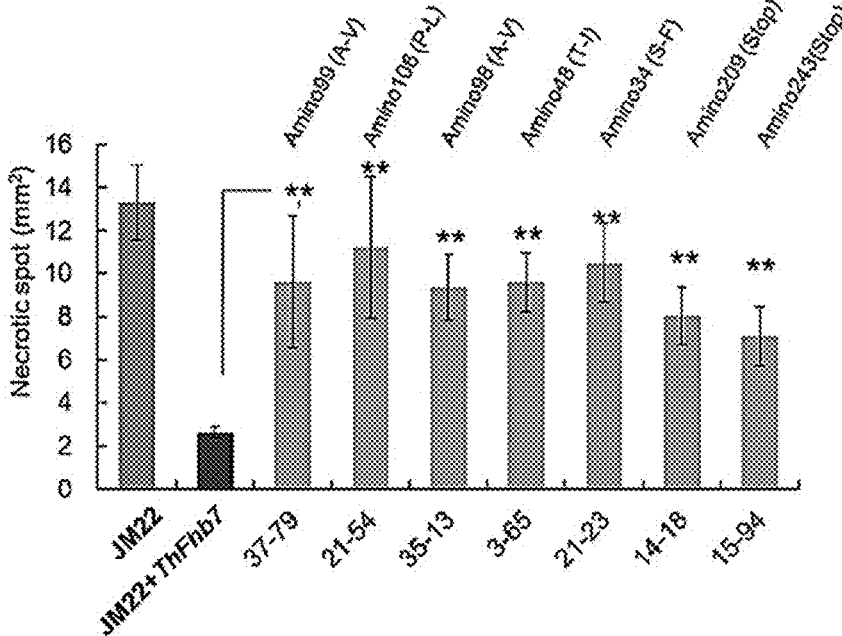
FIG. 9 shows the identification result of phenotype of resistance of mutants to Fusarium head blight.

The results of phenotype identification of resistance of mutants to Fusarium head blight were shown in FIG. 9. EMS mutagenesis was performed on wheat lines comprising ThFhb7. Ex-vivo leaves were used for assessment of resistance to Fusarium head blight, and the results showed that a total of 7 mutants with amino acid changes in the CDS region were significantly different from the disease-resistant control. The area of necrotic spots was calculated 3 days after inoculation, and at least 10 ex-vivo leaves were used in the detection of each sample.

After UNG enzyme treatment combined with targeted preamplification using dUTPs to eliminate residual contaminants and false positives, 24 mutants were finally selected. Resistance to Fusarium head blight was assessed using ex-vivo leaves. Among the 7 mutants of ThFhb7 gene that were significantly different from the disease-resistant control, there were 5 missense mutations and 2 termination mutations; although there were some differences in the degree of disease-susceptibility of the 7 mutants, the spot areas thereof were significantly larger than the spot area of the disease-resistant control (see the area data of the necrotic spots of the mutants in FIG. 9). After functional analysis, the original epoxy group-removing activity was retained to varying degrees in the 24 mutants. The termination mutations were located at the C-terminal of ThFhb7, terminating at amino acids 209 and 243, respectively, but the two termination mutations would not lead to complete loss of the enzyme's function. Therefore, it was suggested that the functional domain of this enzyme was mainly at the N-terminal. In addition, the 5 missense mutations at positions 34, 48, 98, 99 and 106 in the mutants had a greater impact on the epoxy group-removing activity. Therefore, these amino acids can be identified as critical amino acids.

Example 5

This example is the functional analysis of the gene of homologous sequences.

1. Sequence Alignment

Figure 10:
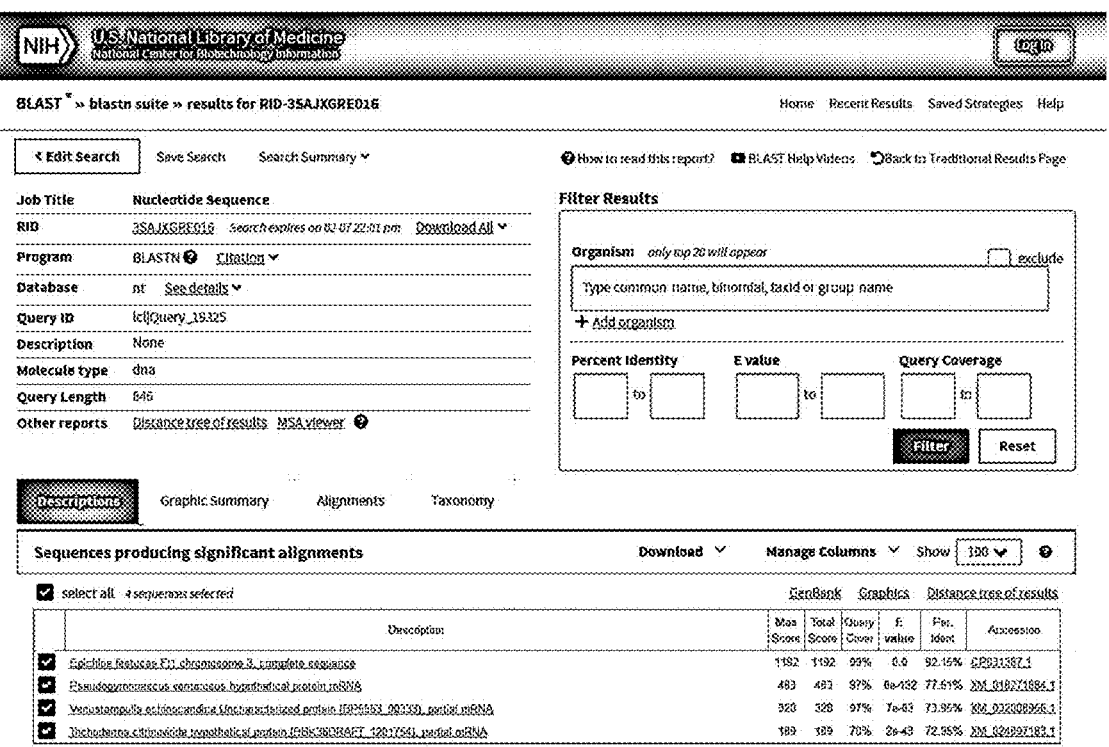
FIG. 10 shows the NCBI alignment results of ThFhb7.
Figure 11:
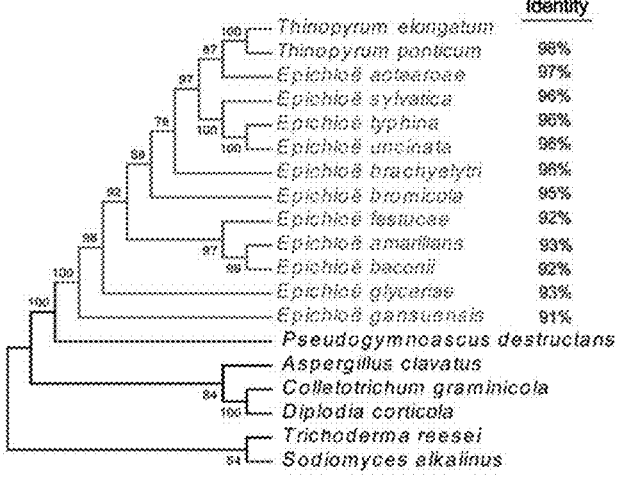
FIG. 11 shows a phylogenetic tree of ThFhb7 and its homologous sequences.
Figure 12:
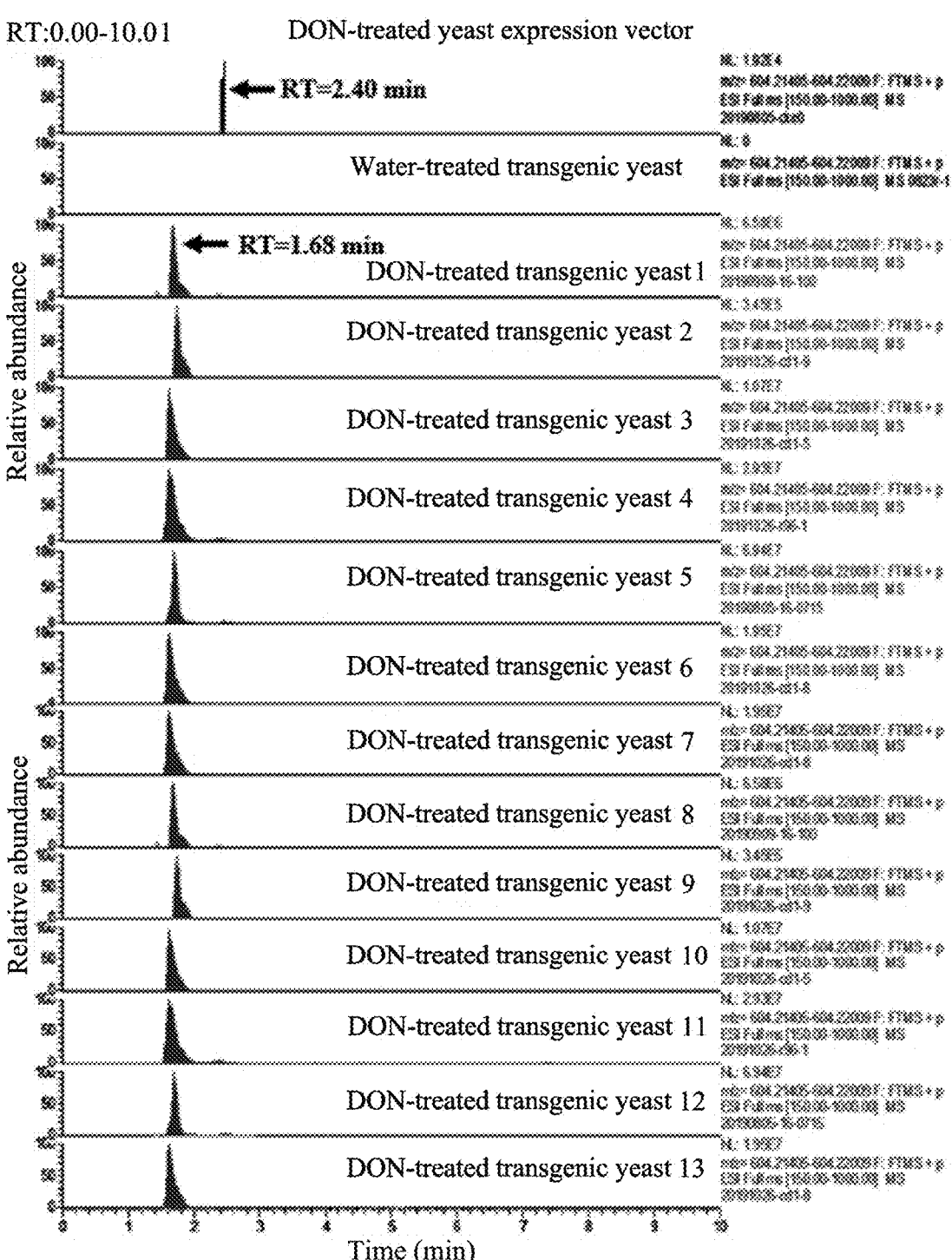
FIG. 12 shows extracted ion chromatograms of DON-treated transgenic yeast by LC-HRMS.

On the basis of the sequence (SEQ ID NO: 1) of the de-epoxidase gene of *Thinopyrum*, blastn alignment was performed by NCBI, and no annotated highly homologous gene was found under default parameters. The NCBI alignment results were shown in FIG. 10. However, according to the information that there were homologous genes among *Epichloë* sp., the inventors jointly searched the genome databases of other laboratories and obtained 11 sequences derived from this genus, set forth in SEQ ID NOs: 25-35 respectively. As shown in FIG. 11, these sequences shared a sequence identity of 90% or more with the de-epoxidase gene of *Thinopyrum ponticum*. In addition, the inventors also isolated a gene from *Thinopyrum elongatum* with a sequence identity of 98% to the de-epoxidase gene of *Thinopyrum ponticum*, and its sequence was set forth in SEQ ID NO: 2.

2. Experiments of Studying Toxins and their Derivatives in *Pichia pastoris* to which the Homologous Sequences of ThFhb7 Gene was Transferred 11 homologous sequences of the gene were obtained from *Epichloë* sp., and the sequences were verified to be correct by sequencing. The yeast expression vectors for the homologous sequences were constructed using pPICZαA-ThFhb7. The recombinant plasmids were then linearized with Sac I, and 1 ml of single-stranded DNA sample was boiled for 5 minutes and then rapidly cooled on ice. The samples were kept on ice. Competent yeast cells were centrifuged, and LiCl was removed with a pipette. For each transformation, the following reagents were added in the order given to the cells. PEG protected cells from the harmful effects of a high concentration of LiCl. Each tube was vortexed vigorously until the cell pellet was completely mixed (for about 1 minute). The test tubes were incubated at 30° C. for 30 minutes and underwent a thermal shock in a water bath at 42° C. for 20 to 25 minutes. Cells were pelleted by centrifugation at 6,000 to 8,000 rpm. The pellet was resuspended in 1 ml of YPD and incubated at 30° C. with oscillation. After 1 hour and 4 hours, 25 to 100 µl were inoculated on the YPD plates comprising an appropriate concentration of Zeocin™. The plates were incubated at 30° C. for 2 to 3 days. 10 single colonies were selected for enrichment culture, yeast chromosomal DNAs were extracted, and positive recombinant cells were detected by PCR. PCR identification was usually performed using pPICZαA universal primers. If the yeast expression vector pPICZαA was used as the template, a target fragment can be amplified; and if the pPICZαA-ThFhb7 homologous sequence was used as the template, a target fragment with a target band size plus 588 bp can be amplified.

3. Expression of Homologous Sequences and Toxin Treatment

The screened positive yeast single colony (X33/pPICZαA-ThFhb7 homologous sequence) and the negative yeast single colony (X33/pPICZαA) were respectively inoculated into 25 ml of BMGY medium, and cultured at 28° C. to 30° C. until OD600 was 2 to 6. The culture was centrifuged at 4,000 rpm for 5 min at room temperature, the supernatant was discarded, the cells were collected, the cells were resuspended in 50 ml to 100 ml (0.5% to 1% methanol) BMMY liquid medium to about OD600=1, transferred to a 500 ml Erlenmeyer flask, and cultured at 28° C. to 30° C., and methanol was added every 24 h to a final concentration of 0.5% to maintain induced expression. After 48 h of induction, the culture solution was aliquoted into 5 ml to 15 ml centrifuge tubes, and various trichothecenes were added to a final concentration of 25 μg/ml, the induction was continued for 48 h to 72 h, and the culture were collected for LC-HRMS analysis.

4. LC-HRMS Analysis

The aliquoted samples were centrifuged at 4° C., and the supernatant was discarded. The samples were quickly frozen in liquid nitrogen, a little quartz sand was added, and after grinding with a plastic grinding rod, 1.3 ml of pre-cooled 75% methanol aqueous solution (comprising 0.1% formic acid) was added. The mixture was vibrated for 10 s, sonicated for 30 min at room temperature, and the supernatant was taken and transferred to a new centrifuge tube. The supernatant was concentrated in vacuo to a dry powder. Before injection, the dry powder was resuspended with 100 μL of 20% acetonitrile solution, filtered through a 0.22 μm filter membrane, and transferred to an injection vial for LC-HRMS detection.

Xcalibur 2.1.0 was used for analysis of data of LC-HRMS (/MS). Extracted ion chromatograms (EICs) of toxins and their derivatives were investigated using the extracted chromatographic peak shape, retention time (±0.2 min) and mass (±5 ppm) of the bioconversion products. According to secondary spectra and basic structures of the substances, the neutral loss was analyzed, and chemical structures were inferred.

The corresponding proteins were expressed by transferring these genes into yeast cells respectively and analyzed by LC-HRMS. The experimental results were shown in FIG. 13. Other 12 homologous sequences were transferred into *Pichia pastoris* and treated with DON. LC-HRMS detection showed generation of DON-GSH. In extracted ion chromatograms of DON-treated transgenic yeast by LC-HRMS, the DON-GSH adduct was detected in positive ion mode, with an m/z of 604.21730 (corresponding to [M+H]+, Δ±5 ppm).

Example 6

I. Preparation of the Active Polypeptide of the Invention

1. Materials and Methods

*Escherichia coli* DH5α strain, expression strain BL21 (DE3), prokaryotic expression vector pET-28a (+) and plasmid pMD19-T-ThFhb7 were preserved in our laboratory, wherein plasmid pMD19-T-ThFhb7 contained a de-epoxidase gene derived from *Thinopyrum*, the sequence of which was set forth in SEQ ID NO: 1.

1.2 Experimental Methods 1.2.1 the Recombinant Expression Vector pET28a-ThFhb7 was Constructed by the Following Method.

The primers with NcoI and BamHI restriction sites were designed according to the sequence of expression vector pET28a, and the primer sequences were as follows (underlined sequences indicate the restriction sites):

```
                                    (SEQ ID NO: 49)
Forward primer:
5'-CCATGGCTAGAAATCCACCCATCGTCATCACC-3';

(SEQ ID NO: 50)
Reverse primer:
5'-GGATCCTCTTCACCTCGGCATACTTGTC-3'.
```

PCR amplification was performed using plasmid pMD19-T-ThFhb7 as a template. The amplification product was detected by 1% agarose gel electrophoresis, and a target fragment was recovered by cutting the gel; the target fragment and pET28a vector were digested by double enzymes, NcoI and BamHI, respectively, followed by gel recovery and ligation with T4 ligase; the ligation product was transformed into *Escherichia coli* DH5a, and colony PCR and double digestion identification were performed to obtain a target gene of about 900 bp and pET28a vector backbone of about 5,000 bp. Further sequencing was performed to verify that the sequence and the reading frame of the recombinant expression vector pET28a-ThFhb7 were correct.

1.2.2 Induced Expression of Polypeptides

The recombinant expression vector plasmid pET28a-ThFhb7 was transformed into the competent cells of *Escherichia coli* expression strain BL21 (DE3); after PCR detection, the positive monoclones on transformation plates were picked and inoculated into test tubes containing 50 μg/mL Kana in 3 mL of LB liquid medium and shaken at 37° C. at 220 r/min overnight. The next day, the culture was inoculated into a Kana LB liquid medium and shaken until the OD600 of the bacterial cells was 0.6 to 0.8. 1 mL of the culture was taken out and centrifuged at room temperature for 2 min, the supernatant was discarded, and the bacterial pellet was resuspended in 100 μl of 1× loading buffer. IPTG was added to the remaining culture to a final concentration of 0.5 mM, and the fusion protein was induced to express by shaking at 37° C. at 220 r/min for 4 h. 1 mL of the culture was taken out and centrifuged at 10,000 r/min for 2 min at room temperature, the supernatant was discarded, and the bacterial pellet was resuspended in 100 μl of 1× loading buffer. The remaining culture was centrifuged at 4,000 r/min for 10 min, the supernatant was discarded, and the bacterial pellet was resuspended in PBS; after the resuspension solution was treated by ultrasonication, the supernatant and the pellet were taken and added to the loading buffer to resuspend respectively.

1.2.3 Purification of Polypeptides

The protein solution was purified using Ni column and collected using a low pressure chromatography system and added to a dialysis bag for overnight dialysis against 50 mM Tris-HCl, 0.30 M NaCl, pH 8.0.

The dialyzed product was shaken at 37° C. for 4 h to induce protein expression with 0.5 mmol/L IPTG, and the bacterial cells were collected and resuspended in PBS. After ultrasonication, the supernatant was collected, and the supernatant was purified by a Ni column and a molecular sieve. The results of SDS-PAGE electrophoresis showed that a polypeptide in the form of soluble protein was obtained, with a molecular weight of about 33 kDa, and the purified protein had a single band, indicating that the purification effect was good (see FIG. 13).

II. Establishment of an In Vitro Enzymatic Reaction System of Polypeptide

1. Experimental Methods 1.1 Reagent:

0.5 mg/ml DON: prepared by 1 mg of DON with addition of distilled water to 2 ml, filtered and sterilized.

1.2 Establishment of an In Vitro Enzymatic Reaction System

The optimal conditions for the in vitro enzymatic reaction system of ThFhb7 polypeptide were established by gradient experiments of three different factors affecting the enzymatic reaction:

(1) the gradient of reaction enzyme amounts: 1 μg, 5 μg, 10 μg, 25 μg, and 50 μg;

(2) the pH gradient set with various buffers: ranging from 3.0 to 10.0, disodium hydrogen phosphate-citric acid buffer (pH=3.0, 4.0, 5.0), disodium hydrogen phosphate-potassium dihydrogen phosphate buffer (pH=6.0, 7.0), and Tris-phosphate buffer (pH=8.0, 9.0, 10.0); and (3) the gradient of reaction temperatures: 4° C., 12° C., 15° C., 20° C., 25° C., 30° C., 37° C., 45° C., and 50° C.

2. Experimental Results 2.1 Effect of Enzyme Amount on the Enzymatic Reaction System The reaction was performed in a phosphate buffer (PBS) (pH=7.0), at 25° C. for 12 h, and samples were taken at 0 h, 0.5 h, 1 h, 3 h, and 6 h respectively for LC-HRMS analysis; through the area results of first-level scanning of LC-HRMS, the changes in the amounts of the two substances, DON as the reaction substrate and the GSH adduct as the reaction product, were obtained with proceeding of reaction, so as to obtain the optimal enzyme amount for the reaction, as shown in FIGS. 14A and 14B.

The experimental results obtained by changing the enzyme amount showed that when the enzyme amount was 1 to 25 μg, the amount of DON-GSH produced was positively correlated with the amount of enzyme added within the same time period. When the enzyme amount exceeded 25 μg, the amount of DON-GSH produced tended to be stable. Therefore, 25 μg was chosen as the optimal test enzyme amount.

2.2 Effect of pH of the Reaction System on the Enzymatic Reaction System

The experimental results of the pH gradient of the enzymatic reaction buffer were shown in FIGS. 15A and 15B. FIGS. 15A and 15B showed that when the pH of the buffer was 6.0, the amount of the product DON-GSH reached the highest value, while the amounts of the reaction substrate DON was the lowest, and thus the suitable pH of the buffer was between 5.0 and 7.0.

3. Effect of Reaction Temperature on the Enzymatic Reaction System

According to the above experimental results, under the conditions at the pH of the reaction buffer of 7.0 and the addition amount of enzyme of 25 μg, the temperatures were set at 4° C., 12° C., 15° C., 20° C., 25° C., 30° C., 37° C., 45° C., and 50° C., and the reaction time was 24 h; samples were taken at 0 h, 0.5 h, 1 h, 6 h, 12 h, and 24 h respectively for LC-HRMS analysis; through the area results of first-level scanning of LC-HRMS, the changes in the amounts of the two substances, DON as the reaction substrate and the GSH adduct as the reaction product, were obtained with proceeding of reaction, so as to obtain the optimal temperature for the reaction.

Figures 16A, 16B, 17A:
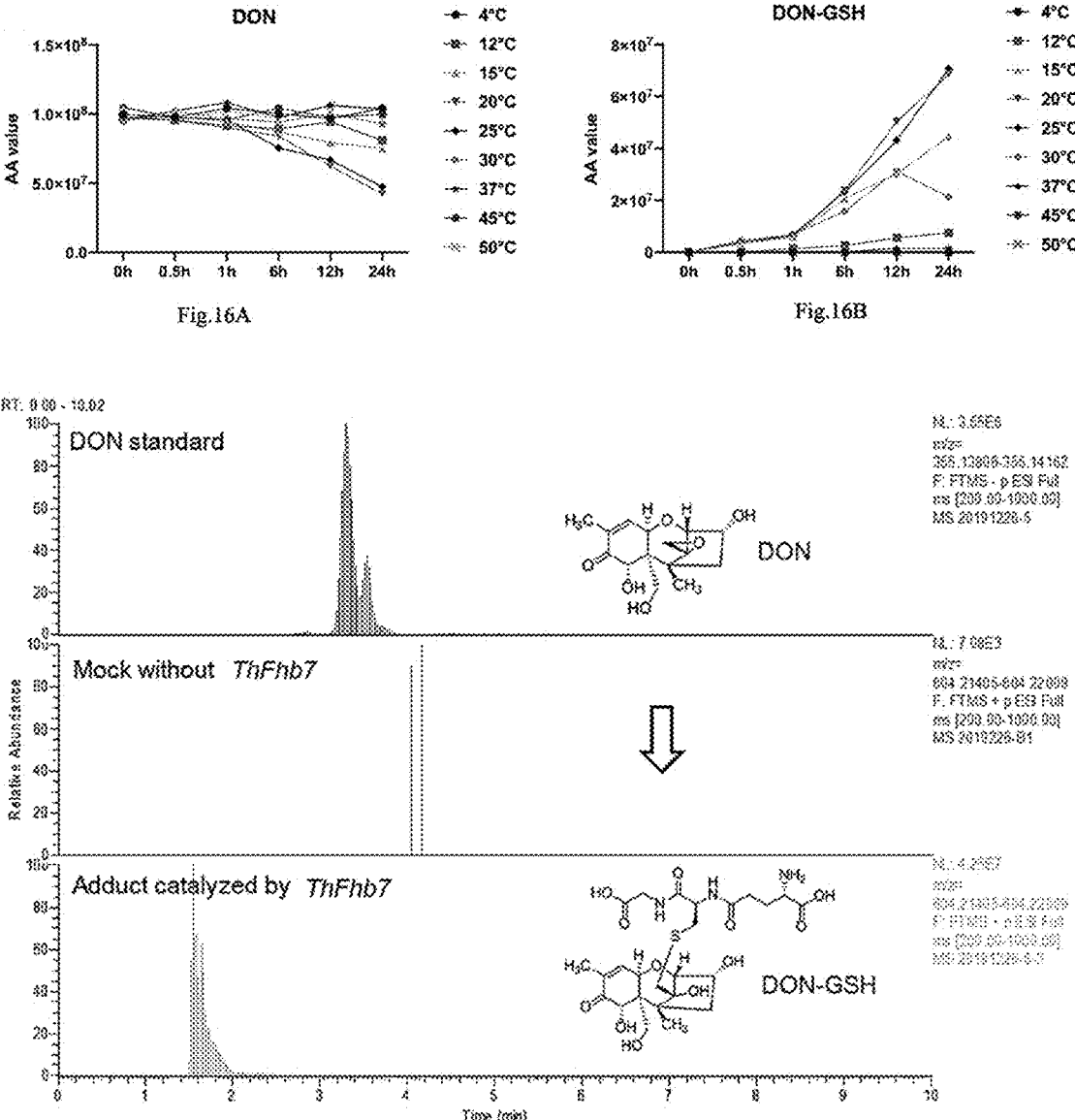
FIGS. 16A and 16B show the effect of the reaction temperature on the enzymatic reaction. Panel
FIG. 17A shows extracted ion chromatograms (EICs) of in vitro enzymatic reaction of DON and GSH by LC-HRMS (Method 1).

The results of experiments obtained by setting different reaction temperatures were shown in FIGS. 16A and 16B. FIGS. 16A and 16B showed that the difference in the effect on the enzymatic reaction was not significant at 20° C. to 25° C., and the amount of the product can all reach the maximum value; the amount of DON-GSH produced decreased with decreasing temperature below 15° C.; the amount of DON-GSH produced was inversely correlated with the increase of reaction temperature at 30° C. to 37° C.; the product DON-GSH cannot be detected by first-level scanning of LC-HRMS above 37° C., indicating that the proteinic enzyme had basically lost its activity. Therefore, the condition at 20° C. to 25° C. was more suitable for the enzymatic reaction.

The above experimental results showed that the most suitable conditions for the proteinic enzyme to carry out in vitro enzymatic reaction were as follows: in the reaction system, 25 μg of purified ThFhb7 protein was added, and after adding an appropriate amount of reaction substrates, the system was supplemented to 200 μl with a buffer at a pH of 5.0 to 7.0, mixed, and reacted at 20° C. to 25° C.

III. Epoxy Group-Removing Reaction of Vomitoxin Catalyzed by the Active Polypeptide

1. Experimental Methods 1.1 In Vitro Enzymatic Reaction:

DON (1 mg) was dissolved in freshly prepared GSH (30.7 mg, 100 μmol) in PBS buffer, and the proteinic enzyme was added, and incubated in a water bath at 20° C. for 24 h.

1.2 LC-HRMS (/MS) Analysis

The in vitro reaction solution was filtered through a 0.22 μm filter membrane and transferred to an injection vial for LC-HRMS detection.

Chromatography was performed on a reverse phase XBridge C18, with an inner diameter of 150×2.1 mm, and a particle size of 3.5 μm (Waters, Dublin, Ireland), at a column temperature of 35° C. The flow rate was 300 μL min$^{-1}$, and the injection volume was 3 μL. Mobile phase: A: 0.1% aqueous acetic acid, B: acetonitrile; elution gradient: A=90% at 0 to 0.2 min; A gradually decreased to 10% at 0.2 to 6 min; A=10% at 6 to 8 min; A gradually increased to 90% at 8.1 min; and A=90% at 8.1 to 10 min.

(1) Full scan mode was performed on a Thermo Scientific™ QExactive™ equipped with an electrospray ionization (ESI) source and a UHPLC system (Accela, Thermo Fisher Scientific, San Jose, CA, USA). The ESI interface in positive ion mode was set as follows: sheath gas: 40 arbitrary units; auxiliary gas: 10 arbitrary units; capillary voltage: 3.8 kV; and capillary temperature: 350° C. The AGC target was set to 2×e5. The ESI interface in negative ion mode was set to 2.9 kV; sheath gas: 4 arbitrary units; and auxiliary gas: 0 arbitrary unit. The mass spectrometer can rapidly alternate positive and negative scan modes within the range of m/z of 200 to 1000, and the mode resolution was set to 70,000 FWHM.

(2) The liquid chromatography method and chromatographic conditions in Full scan+ddms (first-level full scan+ automatic triggering of second-level) mode were the same as above. In this method, full scan and MS2 scan were used alternately with normalized collision energy set to 20 eV and resolution set to 17,500 during product ion scanning.

(3) PRM mode can be used to quantify the relative abundance of toxins and their derivatives in a sample. After screening of precursor ions in PRM mode, dissociation was induced at normalized collision energy (HCID), followed by a fragment detection of product ions in Orbitrap with a resolution set to 17,500. The acquisition speed in MS/MS was set to 3 spectra per second, and normalized collision energies were used, with collision energies applied (15, 30 and 45 eV) being dependent on the specific analyte.

Xcalibur 2.1.0 (Thermo Fisher Scientific, San Jose, CA, USA) were used for analysis of data of LC-HRMS (/MS). Extracted ion chromatograms (EICs) of toxins and their derivatives were investigated using the extracted chromatographic peak shape, retention time (+0.2 min) and mass (+5 ppm) of the bioconversion products. According to secondary spectra and basic structures of the substances, the neutral loss was analyzed, and chemical structures were inferred.

2. Experimental Results

FIG. 17A shows extracted ion chromatograms (EICs) of in vitro enzymatic reaction of DON and GSH by LC-HRMS (Method 1). As shown in FIG. 5A, the extracted ion chromatograms (EICs) of DON were obtained by LC-HRMS (Full scan mode) in negative ion mode, with an m/z of 355.13984 (corresponding to $[M+CH_3COO]^-$ form, $\Delta \pm 5$ ppm); the DON-GSH adduct was detected in positive ion mode, with an m/z of 604.21707 (corresponding to $[M+H]^+$, $\Delta \pm 5$ ppm).

Figure 17B:
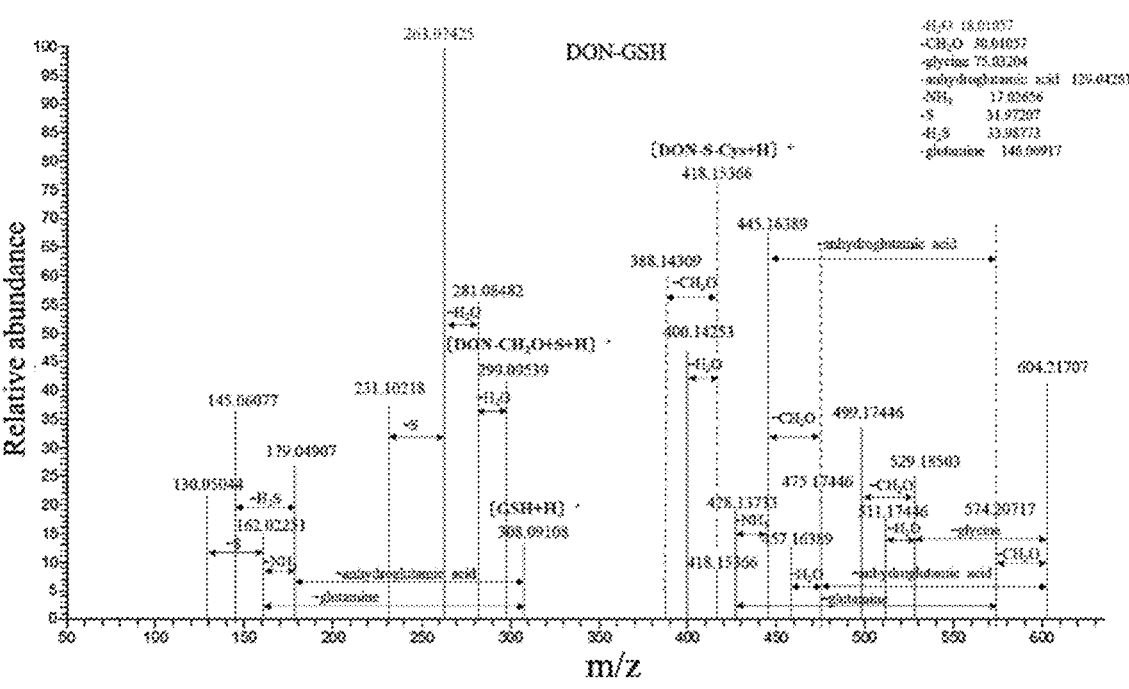
FIG. 17B shows an LC-HRMS2 (Method 2) mass spectrogram of the product ions produced by the high-energy collision induced dissociation of DON-GSH obtained by in vitro enzymatic reaction of DON and GSH.

FIG. 17B shows an LC-HRMS$_2$ (Method 2) mass spectrogram of the product ions produced by the high-energy collision induced dissociation of DON-GSH obtained by in vitro enzymatic reaction of DON and GSH, in $[M+H]^+$ (m/z 604.21707, $\Delta \pm 5$ ppm). The MS fragment of the DON-GSH epoxy adduct was investigated by targeted HRMS$_2$ analysis of positively charged ($[M+H]^+$) ions. Ion fragmentation of DON-GSH yielded a characteristic ion with an m/z of 299.0939, corresponding to $C_{14}H_{19}O_5S^+$. This characteristic ion can be attributed to cleavage of the side chain at C-6 and loss of GSH moiety other than S. This fragment can also be further cleaved to yield ions with m/z ratios of 281.08482 ($C_{14}H_{17}O_4S^+$), 263.07425 ($C_{14}H_{15}O_3S^+$) and 231.10218 ($C_{14}H_{15}O_3^+$). The product ion with an m/z of 263.07425 was the base peak of the HRMS$_2$ mass spectrogram, and this product ion was generated by removing two molecules of $H_2O$ based on the ion with an m/z of 299.0939.

DON-GSH can generate a fragment ion with an m/z of 529.18503 ($C_{23}H_{33}O_{10}N_2S^+$) after the loss of glycine, and also generate a fragment ion with an m/z of 475.17466 ($C_{20}H_{31}ON_2S^+$) after the loss of anhydroglutamic acid. The ion fragment with the side chain at C-6 lost, with an m/z of 574.20717 ($C_{24}H_{36}O_{11}N_3S^+$), can generate a characteristic ion ($C_{19}H_{29}O_8N_2S^+$) with an m/z of 445.16389 after the loss of anhydroglutamic acid from the GSH moiety; and can also generate an ion with an m/z of 428.13733 ($C_{19}H_{26}O_8NS^+$) after removing glutamine.

The product ion had an m/z of 308.09108 ($C_{10}H_{18}O_6N_3S^+$, corresponding to $[M+H]^+$ of GSH). This fragment ion lost anhydroglutamic acid to obtain an ion with an m/z of 179.04907 ($C_5H_{11}O_3N_2S^+$); and lost glutamine to obtain an ion with an m/z of 162.02251 ($C_5H_2O_3NS^+$). In addition, the product ions with m/z ratios of 130.05044 ($C_5H_8O_3N^+$) and 145.06077 ($C_5H_2O_3N_2^+$) were associated with GSH.

3. Experimental Conclusion

The active polypeptide of the invention can efficiently catalyze vomitoxin into a glutathione adduct in vitro, and it can be seen from the secondary spectrum that the formation of the adduct destroyed the epoxy ring structure playing a major role in the toxicity, which can greatly reduce the toxicity of the toxin.

IV. Cytotoxicity Test of Vomitoxin-GSH Derivatives

1. Cell Culture

Using a DMEM basal medium supplemented with 10% fetal bovine serum and 500 μl of penicillin-streptomycin (double antibiotics), the pancreatic cancer cell line (PATU8988), human embryonic kidney cell 293-derived line (293T) and normal human esophageal epithelial cells (HEECs) were cultured in a thermostatic incubator with 5% $CO_2$ at 37° C. When the cells grew to 80% to 90% adherent to the wall of the flask, they were subcultured every 2 to 3 d, and the cells were collected by trypsinization and subcultured. According to the cell growth state, cells at the logarithmic growth stage were selected for experiments.

2. Cytotoxicity Assay by CCK8 Method

The Cell Counting Kit-8 (CCK-8 for short) reagent can be used to easily and accurately analyze cell proliferation and cytotoxicity. The three cell lines at the logarithmic growth stage were inoculated into 96-well plates with 100 μl (about $5 \times 10^3$ cells) per well and were routinely cultured for 24 h at 37° C. with 5% $CO_2$. The medium was discarded and grouped. Wells were set in triplicate for each group for observation, and the treatment methods of each group were as follows: the blank group was the zero-adjustment well containing medium only, the control group was the DMEM medium containing 10% fetal bovine serum, and gradients of low, medium and high concentrations were all set for DON and its corresponding glutathione adduct produced by the enzymatic reaction. After culturing at 37° C. for 48 h, 10 μl of CCK8 solution was added to each well to continue the culture. After 2 h, the culture supernatants in the wells were carefully pipetted and discarded, the OD value of each well was measured by a full-wavelength multi-functional microplate reader at a wavelength of 450 nm, and the cell viability was calculated.

3. Experimental Results

The cells were plated at a concentration of $5 \times 10^7$ $L^{-1}$, and the OD450 values for the pancreatic cancer cell line, human embryonic kidney cell 293-derived line and normal human esophageal epithelial cells were detected using a CCK-8 microplate reader after 48 h treatment with DON and its corresponding glutathione adduct produced by the enzymatic reaction. Wells were set in triplicate for each group for observation, and the treatment methods of each group were as follows: the blank group was the zero-adjustment well containing medium only, the control group was the DMEM medium containing 10% fetal bovine serum, and DON and its corresponding glutathione adduct produced by the enzymatic reaction were provided at corresponding concentrations according to the results in literatures for treatment. The results were shown in FIG. 18.

Figure 18:
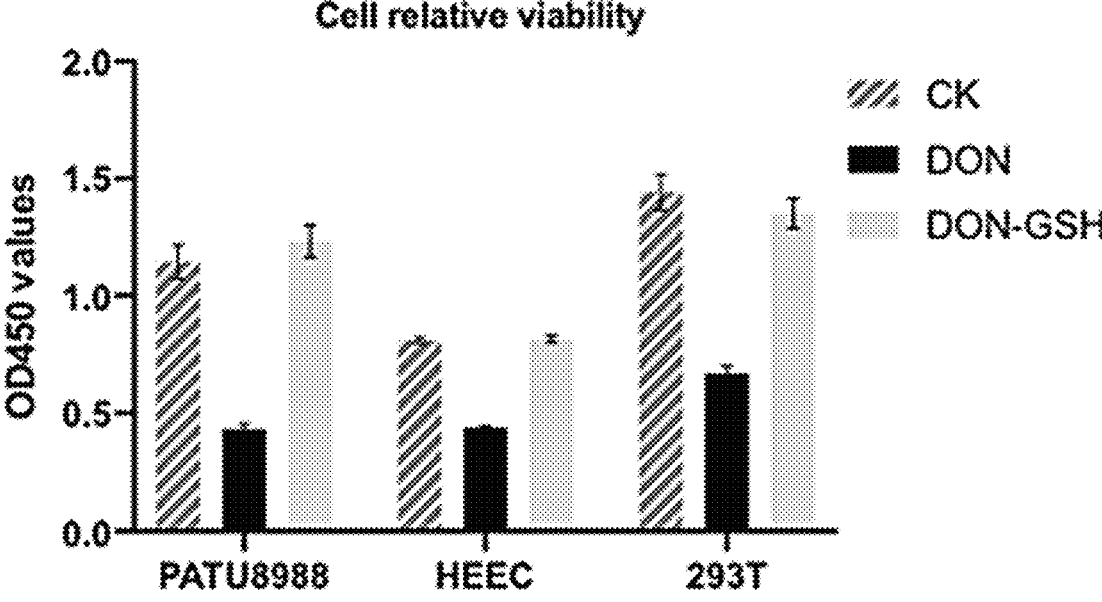
FIG. 18 shows the effect of vomitoxin on cell viability. OD values at 450 nm were measured after cells were treated with different concentrations of DON (a) for 48 h.

It can be seen from the results in FIG. 18 that the cell viability of the pancreatic cancer cell line, human embryonic kidney cell 293-derived line and normal human esophageal epithelial cells decreases sharply after treatment with DON at corresponding concentrations for 48 h, indicating that DON was highly toxic to cells; and the cell viability after treatment with the corresponding derivative produced by the reaction at the same concentration was substantially the same as that of the blank control, indicating that the corresponding glutathione adduct of DON had substantially no toxic effect on cells.

V. Research on Host Cells Expressing the Active Polypeptide and its Function

1. Construction of Yeast Expression Plasmid pPICZαA-ThFhb7

The cDNA of the de-epoxidase gene derived from *Thinopyrum* had a length of 865 bp (SEQ ID NO: 1), the sequence did not comprise Bsp119I and XbaI restriction sites, and the primer sequences were designed as follows:

```
                                    (SEQ ID NO: 51)
F:
5'-ATTATTCGAAAGAAATCCACCCATCGTCATCACC-3';

(SEQ ID NO: 52)
R:
5'-TTGTTCTAGACTACTTCACCTCGGCATACTTGTC-3'.
```

The underlined portions are restriction endonuclease sites. The whole gene sequence of the cDNA was obtained by PCR. The PCR product was purified, and digested by double enzymes, Bsp119I and XbaI, and meanwhile the expression vector pPICZαA was digested with these enzymes. The large fragment of the vector and the target gene fragment were recovered respectively, and the recovered fragments were ligated with T4 DNA ligase and transformed into *Escherichia coli* DH5a. After identification by colony PCR, the positive monoclonal bacterial solution was sequenced for verification.

2. Transformation of *Pichia pastoris*

The recombinant plasmids were first linearized with Sac I, and 1 ml of single-stranded DNA sample was boiled for 5 minutes and then rapidly cooled on ice. The samples were kept on ice. Competent yeast cells were centrifuged, and LiCl was removed with a pipette. 240 μl of 50% polyethylene glycol, 36 μl of 1 M LiCl, 25 μl of 2 mg/ml single-stranded DNAs, and plasmid DNAs (5 to 10 μg) in 50 μl of sterile water were sequentially added. Each tube was vortexed vigorously until the cell pellet was completely mixed (for about 1 minute). The test tubes were incubated at 30° C. for 30 minutes and underwent a thermal shock in a water bath at 42° C. for 20 to 25 minutes. Cells were pelleted by centrifugation. The pellet was resuspended in 1 ml of YPD and incubated at 30° C. with oscillation. After 1 hour and 4 hours, 25 to 100 μl were inoculated on the YPD plates comprising an appropriate concentration of Zeocin™. The plates were incubated at 30° C. for 2 to 3 days.

10 single colonies were selected for enrichment culture, yeast chromosomal DNAs were extracted, and positive recombinant cells were detected by PCR. PCR identification was usually performed using pPICZαA universal primers. If the yeast expression vector pPICZαA was used as the template, a target fragment of about 588 bp can be amplified; and if pPICZαA-ThFhb7 was used as the template, a target fragment with a target band size plus 588 bp can be amplified.

3. Enzyme Expression and Toxin Treatment

The screened positive yeast single colony (X33/pPICZαA-ThFhb7) and the negative yeast single colony (X33/pPICZαA) were respectively inoculated into 25 ml of BMGY medium, and cultured at 28° C. to 30° C. until OD600 was 2 to 6. The culture was centrifuged at room temperature, the supernatant was discarded, the cells were collected, the cells were resuspended in BMMY liquid medium to about OD600=1, transferred to a 500 ml Erlenmeyer flask, and cultured at 28° C. to 30° C., and methanol was added every 24 h to a final concentration of 0.5% to maintain induced expression. After 48 h of induction, the culture solution was aliquoted into 5 ml to 15 ml centrifuge tubes, and vomitoxin was added to a final concentration of 25 μg/ml, the induction was continued for 48 h to 72 h, and the culture were collected for LC-HRMS analysis.

At the same time, after the positive yeast single colony (X33/pPICZαA-ThFhb7) and the negative yeast single colony (X33/pPICZαA) were induced for expressing proteins for 48 h, the culture was diluted with the medium at dilutions of 1, ⅕ and ¹⁄₂₀ (initial OD=0.01), and cultured on YPDA solid media with 400 μM DON and without DON for 5 days, and the growth was observed. The tolerances to DON were compared between transgenic yeast overexpressing active polypeptide and transgenic yeast with the blank vector.

4. LC-HRMS

The aliquoted samples were centrifuged, and the supernatant was discarded. The samples were quickly frozen in liquid nitrogen, a little quartz sand was added, and after grinding with a plastic grinding rod, 1.3 ml of pre-cooled 75% methanol aqueous solution (comprising 0.1% formic acid) was added. The mixture was vibrated for 10 s, sonicated for 30 min at room temperature, and the supernatant was taken and transferred to a new centrifuge tube. The supernatant was concentrated in vacuo to a dry powder. Before injection, the dry powder was resuspended with 100 μL of 20% acetonitrile solution, filtered through a 0.22 μm filter membrane, and transferred to an injection vial for LC-HRMS detection. The detection method was the same as above.

5. Experimental Results

5.1 LC-HRMS Results

Figure 19:
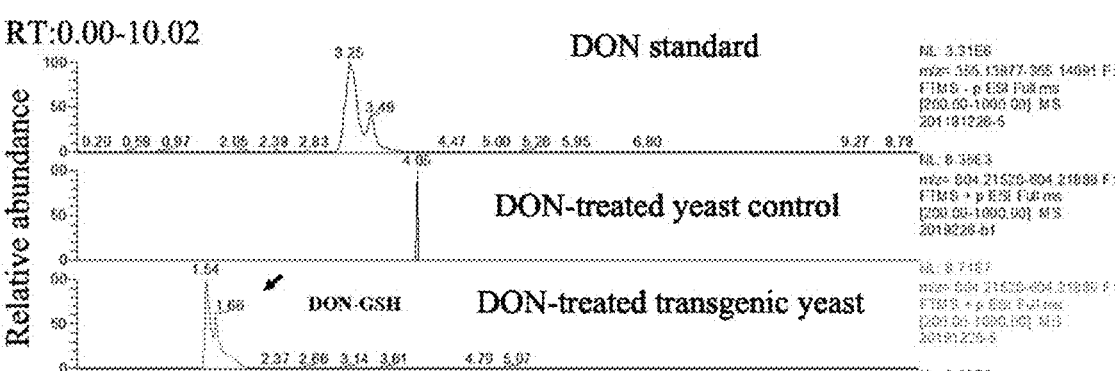
FIG. 19 shows extracted ion chromatograms of toxin-treated transgenic yeast by LC-HRMS (Method 1).

The LC-HRMS results were shown in FIG. 19. The DON-GSH adduct was detected in positive ion mode by LC-HRMS (Full scan) from DON-treated yeast expressing the active polypeptide, with an m/z of the adduct being 604.21730 (corresponding to [M+H]$^+$, Δ±5 ppm).

The results of LC-HRMS detection showed that transfer of the de-epoxidase gene into *Pichia pastoris* can achieve efficient catalysis of conversion of vomitoxin to a glutathione adduct. Transgenic yeast had improved ability of toxin tolerance, demonstrating that ThFhb7 can take vomitoxin as a substrate and catalyze it into the corresponding GSH adduct, thereby playing a role in detoxification in vivo.

5.2 Experimental Results of DON Tolerance of Transgenic Yeast

Figure 20:
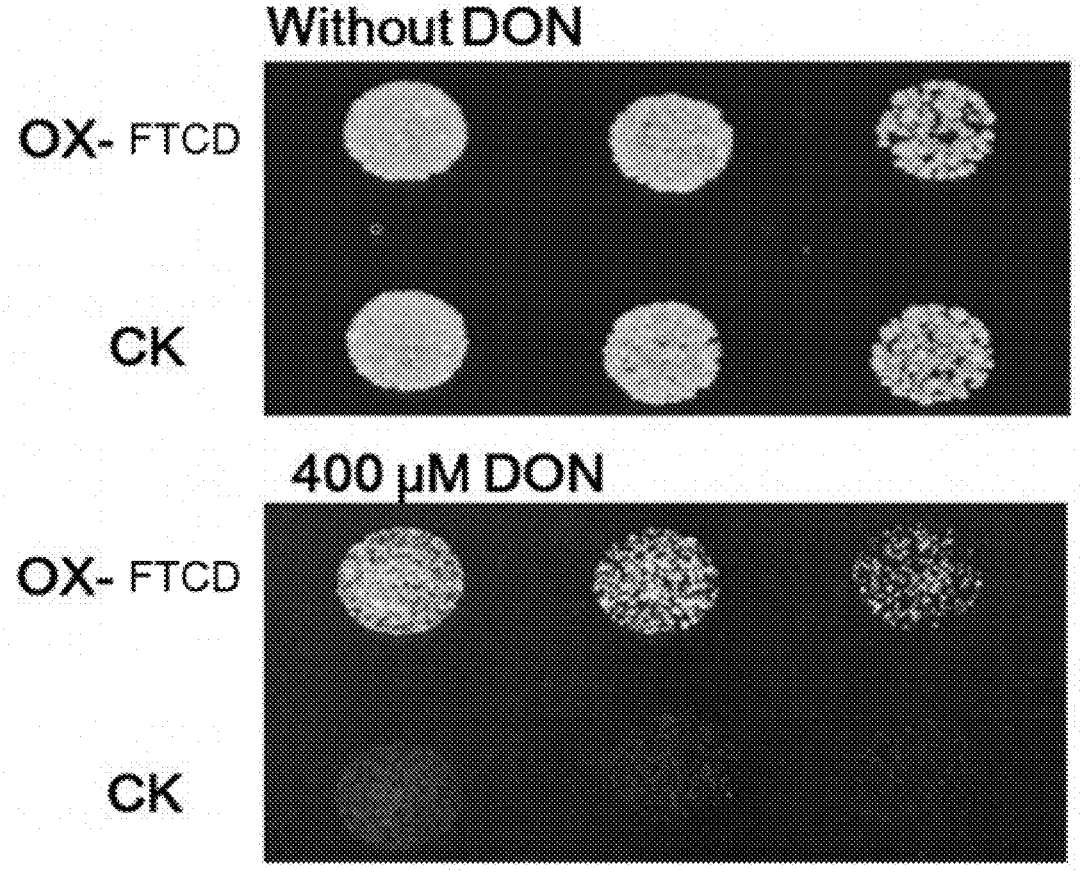
FIG. 20 shows the DON tolerance results of transgenic *Pichia pastoris*.

The growth viabilities of transgenic yeast overexpressing ThFhb7 and transgenic yeast with the blank vector were compared on YPDA media with/without DON. A series of 1, ⅕, and ¹⁄₂₀-fold dilutions of yeast cultures with induced protein expression were added to yeast media (initial OD=0.01), and grown at 30° C. for 5 days, and the growth was observed. The results were shown in FIG. 20. It was found that the growth viability of transgenic yeast overexpressing ThFhb7 on DON-containing media was significantly higher than that of transgenic yeast with the blank vector.

In the DON tolerance experiment of transgenic yeast, it was found that on the YPDA media comprising 400 µM DON, the growth viability of the transgenic yeast comprising ThFhb7 was significantly higher than that of the transgenic yeast with the blank vector, further indicating that ThFhb7 can be expressed in yeast and can catalyze the reaction between glutathione and DON for detoxification, thereby improving the tolerance of yeast to DON.

Although the invention has been described with reference to the exemplary embodiments, it should be understood that the invention is not limited to the disclosed exemplary embodiments. Without departing from the scope or spirit of the invention, various adjustments or changes can be made to the exemplary embodiments of the present specification. The scope of the claims should be based on the broadest interpretation to cover all modifications and equivalent structures and functions.

The invention claimed is:

1. A method for plant transgenesis so as to control a disease, comprising: introducing a nucleic acid into a host plant; allowing the nucleic acid to be expressed, and thereby obtaining a polypeptide; expressing the polypeptide and thereby controlling diseases caused by infection with *Fusarium* species, wherein the nucleic acid molecule has a sequence selected from the group consisting of the following (a) and (b): (a) a sequence as set forth in SEQ ID NO: 1; and (b) a sequence that is codon-optimized for expression in the host plant, having 90% or more sequence identity to (a), and encoding a polypeptide having an amino acid sequence as set forth in SEQ ID NO: 36, wherein the host plant is wheat or maize receiving the introduced nucleic acid.

2. The method according to claim 1, wherein the plant is selected from the group consisting of *Zea mays* and *Triticum aestivum*.

3. A plant cell, comprising an exogenous nucleic acid molecule introduced by means of genetic engineering, wherein the exogenous nucleic acid molecule has a sequence selected from the group consisting of the following (a) and (b): (a) a sequence as set forth in SEQ ID NO: 1; and (b) a sequence that is codon-optimized for expression in the host plant, having 90% or more sequence identity to (a), and encoding a polypeptide having an amino acid sequence as set forth in SEQ ID NO:36, wherein the host plant is wheat or maize.

* * * * *

SEQUENCE LISTING

```
<160> NUMBER OF SEQ ID NOS: 52

<210> SEQ ID NO 1
<211> LENGTH: 846
<212> TYPE: DNA
<213> ORGANISM: Thinopyrum ponticum

<400> SEQUENCE: 1
atggccacct ccgcctccac ctccacccca atcatcttct acgacatagc ccagcggccc      60
cccgtcgcag aaacatgctg cgccgtcaac ccttggaaat ccagactggc cctcaacttc     120
aaggccgtcc cctacacaac cacctgggtg aagatgccag acatcagcag cgtccgcgcc     180
agcctcaacg tgccagcgtg tcgcaagttc gccgacggct ccgacttcaa caccctgccc     240
atcatccacg accccgcgac cgactccctc gtcggcgact cctttgacat cgccgcctac     300
ctgcagcgca cgtatcccgc ctcgggcgcc ggcgacctct ccccccccca gaagctcgac     360
tacgcagtcg gcagggacat gccgcagctg ctcatcccgc tgtccgagat tcgcgcatca     420
ccagagctcg cagactacgc ccgcttcaac agcaacgttg acgcagcctt taccgcgcac     480
gtgggcctca tggtccacgg acttcccttg gatcctgcca ccgccgacgt gaccaaggcc     540
gagtttgtgc ggcgcgcggg gctctcatcg tgggacgact tggaaatggt tggcgaggcg     600
cgcgacaaga tgatgcagtc cctccgaaac atgctggggg acctggctgc cttgtttcgg     660
aaagatgcga gcgggccgtt cctgttgggg cagagggcca cgtatgcgga catgattgtc     720
ggtggctggt tgcgcatgat gcgggcgacg ttgccggtga gtgagtggca ggaggcgaga     780
gcctgccacg gagctatctt tgggcagctg catgatgcgc tggacaagta tgccgaggtg     840
aagtag                                                                 846

<210> SEQ ID NO 2
<211> LENGTH: 846
<212> TYPE: DNA
<213> ORGANISM: Thinopyrum elongatum

<400> SEQUENCE: 2
atggccacct ccacctccac ctccacccca atcatcttct acgacatagc ccagcggccc      60
cccgtcgcag aaacatgctg cgccgtcaac ccttggaaat ccagactggc cctcaacttc     120
aaggccgtcc cctacacaac cacctgggtc aagatgccag atatcagcag cgtccgcgcc     180
agcctcaacg tgccagcgtg tcgcaagttc gccgacggct ccgacttcaa caccctgccc     240
atcatccacg accccgcgac cgactccctc atcggcgact ccttggacat cgccgcctac     300
ctgcagcgca cgtatcccgc ctcgggcgcc ggcgacctct ccccccccca gaagctcgac     360
```

```
tacgcagtcg gcagggacat gcagcagctg ctcttcccgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
gagtttgtgc ggcgcgcggg gctctcatcg tgggacgact tggaaatggt tggcgaggcg      600
cgcgacaaga tgatgcagtc cctccgaaac atgctggggg acctggctgc tttgtttcgg      660
aaagatgcga gcgggccgtt cctgttgggg cagagggcca cgtatgcgga catgattgtc      720
ggtggctggt tgcgcatgat gcgggcgacg ttgccggtga gcgagtggca ggaggcgaga      780
gcctgccacg gggctatctt tgggcagctg catgatgcgc tggacaagta tgccgaggtg      840
aagtag                                                                  846
```

<210> SEQ ID NO 3
<211> LENGTH: 846
<212> TYPE: DNA
<213> ORGANISM: Thinopyrum ponticum

<400> SEQUENCE: 3

```
atggccacct ccgcctccac ctccacccca atcatcttct acgacatagc ccagcggccc       60
cccgtcgcag aaacatgctg cgccgtcaac ccttggaaat ccagactggc cctcaacttc      120
aaggccgtcc cctacacaac cacctgggtg aagatgccag acatcagcag cgtccgcgcc      180
agcctcaacg tgccagcgtg tcgcaagttc gccgacggct ccgacttcaa caccctgccc      240
atcatccacg accccgcgac cgactccctc gtcggcgact cctttgacat cgccgtctac      300
ctgcagcgca cgtatcccgc ctcgggcgcc ggcgacctct ccccccccca gaagctcgac      360
tacgcagtcg gcagggacat gccgcagctg ctcatcccgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
gagtttgtgc ggcgcgcggg gctctcatcg tgggacgact tggaaatggt tggcgaggcg      600
cgcgacaaga tgatgcagtc cctccgaaac atgctggggg acctggctgc cttgtttcgg      660
aaagatgcga gcgggccgtt cctgttgggg cagagggcca cgtatgcgga catgattgtc      720
ggtggctggt tgcgcatgat gcgggcgacg ttgccggtga gtgagtggca ggaggcgaga      780
gcctgccacg gagctatctt tgggcagctg catgatgcgc tggacaagta tgccgaggtg      840
aagtag                                                                  846
```

<210> SEQ ID NO 4
<211> LENGTH: 846
<212> TYPE: DNA
<213> ORGANISM: Thinopyrum ponticum

<400> SEQUENCE: 4

```
atggccacct ccgcctccac ctccacccca atcatcttct acgacatagc ccagcggccc       60
cccgtcgcag aaacatgctg cgccgtcaac ccttggaaat ccagactggc cctcaacttc      120
aaggccgtcc cctacacaac cacctgggtg aagatgccag acatcagcag cgtccgcgcc      180
agcctcaacg tgccagcgtg tcgcaagttc gccgacggct ccgacttcaa caccctgccc      240
atcatccacg accccgcgac cgactccctc gtcggcgact cctttgacat cgccgcctac      300
ctgcagcgca cgtatctcgc ctcgggcgcc ggcgacctct ccccccccca gaagctcgac      360
tacgcagtcg gcagggacat gccgcagctg ctcatcccgc tgtccgagat tcgcgcatca      420
```

-continued

```
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
gagtttgtgc ggcgcgcggg gctctcatcg tgggacgact tggaaatggt tggcgaggcg      600
cgcgacaaga tgatgcagtc cctccgaaac atgctggggg acctggctgc cttgtttcgg      660
aaagatgcga gcgggccgtt cctgttgggg cagagggcca cgtatgcgga catgattgtc      720
ggtggctggt tgcgcatgat gcgggcgacg ttgccggtga gtgagtggca ggaggcgaga      780
gcctgccacg gagctatctt tgggcagctg catgatgcgc tggacaagta tgccgaggtg      840
aagtag                                                                  846
```

```
<210> SEQ ID NO 5
<211> LENGTH: 846
<212> TYPE: DNA
<213> ORGANISM: Thinopyrum ponticum

<400> SEQUENCE: 5
```

```
atggccacct ccgcctccac ctccaccccca atcatcttct acgacatagc ccagcggccc       60
cccgtcgcag aaacatgctg cgccgtcaac ccttggaaat ccagactggc cctcaacttc      120
aaggccgtcc cctacacaac cacctgggtg aagatgccag acatcagcag cgtccgcgcc      180
agcctcaacg tgccagcgtg tcgcaagttc gccgacggct ccgacttcaa caccctgccc      240
atcatccacg accccgcgac cgactccctc gtcggcgact cctttgacat cgtcgcctac      300
ctgcagcgca cgtatcccgc ctcgggcgcc ggcgacctct ccccccccca gaagctcgac      360
tacgcagtcg gcagggacat gccgcagctg ctcatcccgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
gagtttgtgc ggcgcgcggg gctctcatcg tgggacgact tggaaatggt tggcgaggcg      600
cgcgacaaga tgatgcagtc cctccgaaac atgctggggg acctggctgc cttgtttcgg      660
aaagatgcga gcgggccgtt cctgttgggg cagagggcca cgtatgcgga catgattgtc      720
ggtggctggt tgcgcatgat gcgggcgacg ttgccggtga gtgagtggca ggaggcgaga      780
gcctgccacg gagctatctt tgggcagctg catgatgcgc tggacaagta tgccgaggtg      840
aagtag                                                                  846
```

```
<210> SEQ ID NO 6
<211> LENGTH: 846
<212> TYPE: DNA
<213> ORGANISM: Thinopyrum ponticum

<400> SEQUENCE: 6
```

```
atggccacct ccgcctccac ctccaccccca atcatcttct acgacatagc ccagcggccc       60
cccgtcgcag aaacatgctg cgccgtcaac ccttggaaat ccagactggc cctcaacttc      120
aaggccgtcc cctacacaac catctgggtg aagatgccag acatcagcag cgtccgcgcc      180
agcctcaacg tgccagcgtg tcgcaagttc gccgacggct ccgacttcaa caccctgccc      240
atcatccacg accccgcgac cgactccctc gtcggcgact cctttgacat cgccgcctac      300
ctgcagcgca cgtatcccgc ctcgggcgcc ggcgacctct ccccccccca gaagctcgac      360
tacgcagtcg gcagggacat gccgcagctg ctcatcccgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
```

-continued

```
gagtttgtgc ggcgcgcggg gctctcatcg tgggacgact tggaaatggt tggcgaggcg      600
cgcgacaaga tgatgcagtc cctccgaaac atgctggggg acctggctgc cttgtttcgg      660
aaagatgcga gcgggccgtt cctgttgggg cagagggcca cgtatgcgga catgattgtc      720
ggtggctggt tgcgcatgat gcgggcgacg ttgccggtga gtgagtggca ggaggcgaga      780
gcctgccacg gagctatctt tgggcagctg catgatgcgc tggacaagta tgccgaggtg      840
aagtag                                                                  846
```

<210> SEQ ID NO 7
<211> LENGTH: 846
<212> TYPE: DNA
<213> ORGANISM: Thinopyrum ponticum

<400> SEQUENCE: 7

```
atggccacct ccgcctccac ctccacccca atcatcttct acgacatagc ccagcggccc       60
cccgtcgcag aaacatgctg cgccgtcaac ccttggaaat tcagactggc cctcaacttc      120
aaggccgtcc cctacacaac cacctgggtg aagatgccag acatcagcag cgtccgcgcc      180
agcctcaacg tgccagcgtg tcgcaagttc gccgacggct ccgacttcaa caccctgccc      240
atcatccacg accccgcgac cgactccctc gtcggcgact cctttgacat cgccgcctac      300
ctgcagcgca cgtatcccgc ctcgggcgcc ggcgacctct ccccccccca gaagctcgac      360
tacgcagtcg gcagggacat gccgcagctg ctcatcccgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
gagtttgtgc ggcgcgcggg gctctcatcg tgggacgact tggaaatggt tggcgaggcg      600
cgcgacaaga tgatgcagtc cctccgaaac atgctggggg acctggctgc cttgtttcgg      660
aaagatgcga gcgggccgtt cctgttgggg cagagggcca cgtatgcgga catgattgtc      720
ggtggctggt tgcgcatgat gcgggcgacg ttgccggtga gtgagtggca ggaggcgaga      780
gcctgccacg gagctatctt tgggcagctg catgatgcgc tggacaagta tgccgaggtg      840
aagtag                                                                  846
```

<210> SEQ ID NO 8
<211> LENGTH: 846
<212> TYPE: DNA
<213> ORGANISM: Thinopyrum ponticum

<400> SEQUENCE: 8

```
atggccacct ccgcctccac ctccacccca atcatcttct acgacatagc ccagcggccc       60
cccgtcgcag aaacatgctg cgccgtcaac ccttggaaat ccagactggc cctcaacttc      120
aaggccgtcc cctacacaac cacctgggtg aagatgccag acatcagcag cgtccgcgcc      180
agcctcaacg tgccagcgtg tcgcaagttc gccgacggct ccgacttcaa caccctgccc      240
atcatccacg accccgcgac cgactccctc gtcggcgact cctttgacat cgccgcctac      300
ctgcagcgca cgtatcccgc ctcgggcgcc ggcgacctct ccccccccca gaagctcgac      360
tacgcagtcg gcagggacat gccgcagctg ctcatcccgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
gagtttgtgc ggcgcgcggg gctctcatcg tgggacgact tggaaatggt tggcgaggcg      600
```

-continued

```
cgcgacaaga tgatgcagtc cctctgaaac atgctggggg acctggctgc cttgtttcgg      660
aaagatgcga gcgggccgtt cctgttgggg cagagggcca cgtatgcgga catgattgtc      720
ggtggctggt tgcgcatgat gcgggcgacg ttgccggtga gtgagtggca ggaggcgaga      780
gcctgccacg gagctatctt tgggcagctg catgatgcgc tggacaagta tgccgaggtg      840
aagtag                                                                 846
```

<210> SEQ ID NO 9
<211> LENGTH: 846
<212> TYPE: DNA
<213> ORGANISM: Thinopyrum ponticum

<400> SEQUENCE: 9

```
atggccacct ccgcctccac ctccacccca atcatcttct acgacatagc ccagcggccc       60
cccgtcgcag aaacatgctg cgccgtcaac ccttggaaat ccagactggc cctcaacttc      120
aaggccgtcc cctacacaac cacctgggtg aagatgccag acatcagcag cgtccgcgcc      180
agcctcaacg tgccagcgtg tcgcaagttc gccgacggcc ccgacttcaa caccctgccc      240
atcatccacg accccgcgac cgactccctc gtcggcgact cctttgacat cgccgcctac      300
ctgcagcgca cgtatcccgc ctcgggcgcc ggcgacctct ccccccccca gaagctcgac      360
tacgcagtcg gcagggacat gccgcagctg ctcatcccgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
gagtttgtgc ggcgcgcggg gctctcatcg tgggacgact tggaaatggt tggcgaggcg      600
cgcgacaaga tgatgcagtc cctccgaaac atgctggggg acctggctgc cttgtttcgg      660
aaagatgcga gcgggccgtt cctgttgggg cagagggcca cgtatgcgga catgattgtc      720
ggtggctgat tgcgcatgat gcgggcgacg ttgccggtga gtgagtggca ggaggcgaga      780
gcctgccacg gagctatctt tgggcagctg catgatgcgc tggacaagta tgccgaggtg      840
aagtag                                                                 846
```

<210> SEQ ID NO 10
<211> LENGTH: 846
<212> TYPE: DNA
<213> ORGANISM: Thinopyrum ponticum

<400> SEQUENCE: 10

```
atggccacct ccgcctccac ctccacccca atcatcttct acgacatagc ccagcggccc       60
cccgtcgcaa aaacatgctg cgccgtcaac ccttggaaat ccagactggc cctcaacttc      120
aaggccgtcc cctacacaac cacctgggtg aagatgccag acatcagcag cgtccgcgcc      180
agcctcaacg tgccagcgtg tcgcaagttc gccgacggct ccgacttcaa caccctgccc      240
atcatccacg accccgcgac cgactccctc gtcggcgact cctttgacat cgccgcctac      300
ctgcagcgca cgtatcccgc ctcgggcgcc ggcgacctct ccccccccca gaagctcgac      360
tacgcagtcg gcagggacat gccgcagctg ctcatcccgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
gagtttgtgc ggcgcgcggg gctctcatcg tgggacgact tggaaatggt tggcgaggcg      600
cgcgacaaga tgatgcagtc cctccgaaac atgctggggg acctggctgc cttgtttcgg      660
aaagatgcga gcgggccgtt cctgttgggg cagagggcca cgtatgcgga catgattgtc      720
```

-continued

```
ggtggctggt tgcgcatgat gcgggcgacg ttgccggtga gtgagtggca ggaggcgaga      780
gcctgccacg gagctatctt tgggcagctg catgatgcgc tggacaagta tgccgaggtg      840
aagtag                                                                  846

<210> SEQ ID NO 11
<211> LENGTH: 846
<212> TYPE: DNA
<213> ORGANISM: Thinopyrum ponticum

<400> SEQUENCE: 11
atggccacct ccgcctccac ctccacccca atcatcttct acgacatagc ccagcggccc       60
cccgtcgcag aaacatgctg cgccgtcaac ccttggaaat ccagactggc cctcaacttc      120
aaggccgtcc cctacacaac cacctgggtg aagatgccag acatcagcag cgtccgcgcc      180
agcctcaacg tgccagcgtg tcgcaagttc gccgacggct ccgacttcaa caccctgccc      240
atcatccacg accccgcgac cgactccctc gtcggcgact cctttgacat cgccgcctac      300
ctgcagcgca cgtatcccgc ctcgggcgcc ggcgacctct ccccccccca gaagctcgac      360
tacgcagtcg gcagggacat gccgcagctg ctcatctcgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
gagtttgtgc ggcgcgcggg gctctcatcg tgggacgact tggaaatggt tggcgaggcg      600
cgcgacaaga tgatgcagtc cctccgaaac atgctggggg acctggctgc cttgtttcgg      660
aaagatgcga gcgggccgtt cctgttgggg cagagggcca cgtatgcgga catgattgtc      720
ggtggctggt tgcgcatgat gcgggcgacg ttgccggtga gtgagtggca ggaggcgaga      780
gcctgccacg gagctatctt tgggcagctg catgatgcgc tggacaagta tgccgaggtg      840
aagtag                                                                  846

<210> SEQ ID NO 12
<211> LENGTH: 846
<212> TYPE: DNA
<213> ORGANISM: Thinopyrum ponticum

<400> SEQUENCE: 12
atggccacct ccgcctccac ctccacccca atcatcttct acgacatagc ccagcggccc       60
cccgtcgcag aaacatgctg cgccgtcaac ccttggaaat ccaaactggc cctcaacttc      120
aaggccgtcc cctacacaac cacctgggtg aagatgccag acatcagcag cgtccgcgcc      180
agcctcaacg tgccagcgtg tcgcaagttc gccgacggct ccgacttcaa caccctgccc      240
atcatccacg accccgcgac cgactccctc gtcggcgact cctttgacat cgccgcctac      300
ctgcagcgca cgtatcccgc ctcgggcgcc ggcgacctct ccccccccca gaagctcgac      360
tacgcagtcg gcagggacat gccgcagctg ctcatcccgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
gagtttgtgc ggcgcgcggg gctctcatcg tgggacgact tggaaatggt tggcgaggcg      600
cgcgacaaga tgatgcagtc cctccgaaac atgctggggg acctggctgc cttgtttcgg      660
aaagatgcga gcgggccgtt cctgttgggg cagagggcca cgtatgcgga catgattgtc      720
```

-continued

```
ggtggctggt tgcgcatgat gcgggcgacg ttgccggtga gtgagtggca ggaggcgaga     780
gcctgccacg gagctatctt tgggcagctg catgatgcgc tggacaagta tgccgaggtg     840
aagtag                                                                 846
```

<210> SEQ ID NO 13
<211> LENGTH: 846
<212> TYPE: DNA
<213> ORGANISM: Thinopyrum ponticum

<400> SEQUENCE: 13

```
atggccacct ccgcctccac ctccacccca atcatcttct acgacatagc ccagcggccc      60
cccgtcgcag aaacatgctg cgccgtcaac ccttggaaat ccagactggc cctcaacttc     120
aaggccgtcc cctacacaac cacctgggtg aagatgccag acatcagcag cgtccgcgcc     180
agcctcaacg tgccagcgtg tcgcaagttc gccgacggct ccgacttcaa caccctgccc     240
atcatccacg accccgcgac cgactccttc gtcggcgact cctttgacat cgccgcctac     300
ctgcagcgca cgtatcccgc ctcgggcgcc ggcgacctct ccccccccca gaagctcgac     360
tacgcagtcg gcagggacat gccgcagctg ctcatcccgc tgtccgagat tcgcgcatca     420
ccagagctcg cagactacgc ccgcttcaac agcaacgttg acgcagcctt taccgcgcac     480
gtgggcctca tggtccacgg acttcccttg gatcctgcca ccgccgacgt gaccaaggcc     540
gagtttgtgc ggcgcgcggg gctctcatcg tgggacgact tggaaatggt tggcgaggcg     600
cgcgacaaga tgatgcagtc cctccgaaac atgctgggg  acctggctgc cttgtttcgg     660
aaagatgcga gcgggccgtt cctgttgggg cagagggcca cgtatgcgga catgattgtc     720
ggtggctggt tgcgcatgat gcgggcgacg ttgccggtga gtgagtggca ggaggcgaga     780
gcctgccacg gagctatctt tgggcagctg catgatgcgc tggacaagta tgccgaggtg     840
aagtag                                                                 846
```

<210> SEQ ID NO 14
<211> LENGTH: 846
<212> TYPE: DNA
<213> ORGANISM: Thinopyrum ponticum

<400> SEQUENCE: 14

```
atggccacct ccgcctccac ctccacccca atcatcttct acgacatagc ccagcggccc      60
cccgtcgcag aaacatgctg cgccgtcaac ccttggaaat ccagactggc cctcaacttc     120
aaggccgtcc cctacacaac cacctgggtg aagatgccag acatcagcag cgtccgcgcc     180
agcctcaacg tgccagcgtg tcgcaagttc gccgacggct ccgacttcaa caccctgccc     240
atcatccacg accccgcgac cgactccctc gtcggcgact cctttgacat cgccgcctac     300
ctgcagcgca cgtatcccgc ctcgggcgcc ggcgacctct ccccccccca gaagctcgac     360
tacgcagtcg gcagggacat gccgcagctg ctcatcccgc tgtccgagat tcgcgcatca     420
ctagagctcg cagactacgc ccgcttcaac agcaacgttg acgcagcctt taccgcgcac     480
gtgggcctca tggtccacgg acttcccttg gatcctgcca ccgccgacgt gaccaaggcc     540
gagtttgtgc ggcgcgcggg gctctcatcg tgggacgact tggaaatggt tggcgaggcg     600
cgcgacaaga tgatgcagtc cctccgaaac atgctgggg  acctggctgc cttgtttcgg     660
aaagatgcga gcgggccgtt cctgttgggg cagagggcca cgtatgcgga catgattgtc     720
```

-continued

```
ggtggctggt tgcgcatgat gcgggcgacg ttgccggtga gtgagtggca ggaggcgaga        780
gcctgccacg gagctatctt tgggcagctg catgatgcgc tggacaagta tgccgaggtg        840
aagtag                                                                    846

<210> SEQ ID NO 15
<211> LENGTH: 846
<212> TYPE: DNA
<213> ORGANISM: Thinopyrum ponticum

<400> SEQUENCE: 15
atggccacct ccgcctccac ctccacccca atcatcttct acgacatagc ccagcggccc         60
cccgtcgcag aaacatgctg cgccgtcaac ccttggaaat ccagactggc cctcaacttc        120
aaggccgtcc cctacacaac cacctgggtg aagatgccag acatcagcag cgtccgcgcc        180
agcctcaacg tgccagcgtg tcgcaagttc gccgacggct ccgacttcaa caccctgccc        240
atcatccacg accccgcgac cgactccctc gtcggcgact cctttgacat cgccgcctac        300
ctgcagcgca cgtatcccgc ctcgggcgcc ggcgacctct ccccccccca gaagctcgac        360
tacgcagtcg gcagggacat gccgcagctg ctcatcccgc tgtccgagat tcacgcatca        420
ccagagctcg cagactacgc ccgcttcaac agcaacgttg acgcagcctt taccgcgcac        480
gtgggcctca tggtccacgg acttcccttg gatcctgcca ccgccgacgt gaccaaggcc        540
gagtttgtgc ggcgcgcggg gctctcatcg tgggacgact tggaaatggt tggcgaggcg        600
cgcgacaaga tgatgcagtc cctccgaaac atgctggggg acctggctgc cttgtttcgg        660
aaagatgcga gcgggccgtt cctgttgggg cagagggcca cgtatgcgga catgattgtc        720
ggtggctggt tgcgcatgat gcgggcgacg ttgccggtga gtgagtggca ggaggcgaga        780
gcctgccacg gagctatctt tgggcagctg catgatgcgc tggacaagta tgccgaggtg        840
aagtag                                                                    846

<210> SEQ ID NO 16
<211> LENGTH: 846
<212> TYPE: DNA
<213> ORGANISM: Thinopyrum ponticum

<400> SEQUENCE: 16
atggccacct ccgcctccac ctccacccca atcatcttct acgacatagc ccagcggccc         60
cccgtcgcag aaacatgctg cgccgtcaac ccttggaaat ccagactggc cctcaacttc        120
aaggccgtcc cctacacaac cacctgggtg aagatgccag acatcagcag cgtccgcgcc        180
agcctcaacg tgccagcgtg tcgcaagttc gccgacggct ccgacttcaa caccctgccc        240
atcatccacg accccgcgac cgactccctc gtcggcgact cctttgacat cgccgcctac        300
ctgcagcgca cgtatcccgc ctcgggcgcc ggcgacctct ccccccccca gaagctcgac        360
tacacagtcg gcagggacat gccgcagctg ctcatcccgc tgtccgagat tcgcgcatca        420
ccagagctcg cagactacgc ccgcttcaac agcaacgttg acgcagcctt taccgcgcac        480
gtgggcctca tggtccacgg acttcccttg gatcctgcca ccgccgacgt gaccaaggcc        540
gagtttgtgc ggcgcgcggg gctctcatcg tgggacgact tggaaatggt tggcgaggcg        600
cgcgacaaga tgatgcagtc cctccgaaac atgctggggg acctggctgc cttgtttcgg        660
aaagatgcga gcgggccgtt cctgttgggg cagagggcca cgtatgcgga catgattgtc        720
ggtggctggt tgcgcatgat gcgggcgacg ttgccggtga gtgagtggca ggaggcgaga        780
```

-continued

```
gcctgccacg gagctatctt tgggcagctg catgatgcgc tggacaagta tgccgaggtg      840
aagtag      846

<210> SEQ ID NO 17
<211> LENGTH: 846
<212> TYPE: DNA
<213> ORGANISM: Thinopyrum ponticum

<400> SEQUENCE: 17
atggccacct ccgcctccac ctccacccca atcatcttct acgacatagc ccagcggccc       60
cccgtcgcag aaacatgctg cgccgtcaac ccttggaaat ccagactggc cctcaacttc      120
aaggccgtcc cctacacaac cacctgggtg aagatgccag acatcagcag cgtccgcgcc      180
agcttcaacg tgccagcgtg tcgcaagttc gccgacggct ccgacttcaa caccctgccc      240
atcatccacg accccgcgac cgactccctc gtcggcgact cctttgacat cgccgcctac      300
ctgcagcgca cgtatcccgc ctcgggcgcc ggcgacctct tcccccccca gaagctcgac      360
tacgcagtcg gcagggacat gccgcagctg ctcatcccgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gaccaaggcc      540
gagtttgtgc ggcgcgcggg gctctcatcg tgggacgact tggaaatggt tggcgaggcg      600
cgcgacaaga tgatgcagtc cctccgaaac atgctggggg acctggctgc cttgtttcgg      660
aaagatgcga gcgggccgtt cctgttgggg cagagggcca cgtatgcgga catgattgtc      720
ggtggctggt tgcgcatgat gcgggcgacg ttgccggtga gtgagtggca ggaggcgaga      780
gcctgccacg gagctatctt tgggcagctg catgatgcgc tggacaagta tgccgaggtg      840
aagtag      846

<210> SEQ ID NO 18
<211> LENGTH: 846
<212> TYPE: DNA
<213> ORGANISM: Thinopyrum ponticum

<400> SEQUENCE: 18
atggccacct ccgcctccac ctccacccca atcatcttct acgacatagc ccagcggccc       60
cccgtcgcag aaacatgctg cgccgtcaac ccttggaaat ccagactggc cctcaacttc      120
aaggccgtcc cctacacaac cacctgggtg aagatgccag acatcagcag cgtccgcgcc      180
agcctcaacg tgccagcgtg tcgcaagttc gccgacggct ccgacttcaa caccctgccc      240
atcatccacg accccgcgac cgactccctc gtcggcgact cctttgacat cgccgcctac      300
ctgcagcgca cgtatcccgc ctcgggcgcc ggcgacctct tcccccccca gaagctcgac      360
tacgcagtcg gcagggacat gccgcagctg ctcatcccgc tgtccgagat tcgcgcatca      420
ccagagctcg cagactacgc ccgcttcaac agcaacgttg acgcagcctt taccgcgcac      480
gtgggcctca tggtccacgg acttcccttg gatcctgcca ccgccgacgt gatcaaggcc      540
gagtttgtgc ggcgcgcggg gctctcatcg tgggacgact tggaaatggt tggcgaggcg      600
cgcgacaaga tgatgcagtc cctccgaaac atgctggggg acctggctgc cttgtttcgg      660
aaagatgcga gcgggccgtt cctgttgggg cagagggcca cgtatgcgga catgattgtc      720
ggtggctggt tgcgcatgat gcgggcgacg ttgccggtga gtgagtggca ggaggcgaga      780
gcctgccacg gagctatctt tgggcagctg catgatgcgc tggacaagta tgccgaggtg      840
aagtag      846
```

-continued

```
<210> SEQ ID NO 19
<211> LENGTH: 846
<212> TYPE: DNA
<213> ORGANISM: Thinopyrum ponticum

<400> SEQUENCE: 19
atggccacct ccgcctccac ctccacccca atcatcttct acgacatagc ccagcggccc      60
cccgtcgcag aaacatgctg cgccgtcaac ccttggaaat ccagactggc cctcaacttc     120
aaggccgtcc cctacacaac cacctgggtg aagatgccag acatcagcag cgtccgcgcc     180
agcctcaacg tgccagcgtg tcgcaagttc gccgacggct ccgacttcaa caccctgccc     240
atcatccacg accccgcgac cgactccctc gtcggcgact cctttgacat cgccgcctac     300
ctgcagcgca cgtatcccgc ctcgggcgcc ggcgacctct ccccccccca gaagctcgac     360
tacgcagtcg gcagggacat gccgcagctg ctcatcccgc tgtccgagat tcgcgcatca     420
ccagagctcg cagactacgc ccgcttcaac agcaacgttg acgcagcctt taccgcgcac     480
gtgggcctca tggtccacgg acttcccttg gatcctgcca ccgtcgacgt gaccaaggcc     540
gagtttgtgc ggcgcgcggg gctctcatcg tgggacgact tggaaatggt tggcgaggcg     600
cgcgacaaga tgatgcagtc cctccgaaac atgctggggg acctggctgc cttgtttcgg     660
aaagatgcga gcgggccgtt cctgttgggg cagagggcca cgtatgcgga catgattgtc     720
ggtggctggt tgcgcatgat gcgggcgacg ttgccggtga gtgagtggca ggaggcgaga     780
gcctgccacg gagctatctt tgggcagctg catgatgcgc tggacaagta tgccgaggtg     840
aagtag                                                                 846

<210> SEQ ID NO 20
<211> LENGTH: 846
<212> TYPE: DNA
<213> ORGANISM: Thinopyrum ponticum

<400> SEQUENCE: 20
atggccacct ccgcctccac ctccacccca atcatcttct acgacatagc ccagcggccc      60
cccgtcgcag aaacatgctg cgccgtcaac ccttggaaat ccagactggc cctcaacttc     120
aaggccgtcc cctacacaac cacctgggtg aagatgccag acatcagcag cgtccgcgcc     180
agcctcaacg tgccagcgtg tcgcaagttc gccgacggct ccgacttcaa caccctgccc     240
atcatccacg accccgcgac cgactccctc gtcggcgact cctttgacat cgccgcctac     300
ctgcagcgca cgtatcccgt ctcgggcgcc ggcgacctct ccccccccca gaagctcgac     360
tacgcagtcg gcagggacat gccgcagctg ctcatcccgc tgtccgagat tcgcgcatca     420
ccagagctcg cagactacgc ccgcttcaac agcaacgttg acgcagcctt taccgcgcac     480
gtgggcctca tggtccacgg acttcccttg gatcctgcca ccgccgacgt gaccaaggcc     540
gagtttgtgc ggcgcgcggg gctctcatcg tgggacgact tggaaatggt tggcgaggcg     600
cgcgacaaga tgatgcagtc cctccgaaac atgctggggg acctggctgc cttgtttcgg     660
aaagatgcga gcgggccgtt cctgttgggg cagagggcca cgtatgcgga catgattgtc     720
ggtggctggt tgcgcatgat gcgggcgacg ttgccggtga gtgagtggca ggaggcgaga     780
gcctgccacg gagctatctt tgggcagctg catgatgcgc tggacaagta tgccgaggtg     840
aagtag                                                                 846

<210> SEQ ID NO 21
```

```
<211> LENGTH: 846
<212> TYPE: DNA
<213> ORGANISM: Thinopyrum ponticum

<400> SEQUENCE: 21
atggccacct ccgcctccac ctccacccca atcatcttct acgacatagc ccagcggccc      60
cccgtcgcag aaacatgctg cgccgtcaac ccttggaaat ccagactggc cctcaacttc     120
aaggccgtcc cctacacaac cacctgggtg aagatgccag acatcagcag cgtccgcgcc     180
agcctcaacg tgccagcgtg tcgcaagttc gccgacggct ccgacttcaa caccctgccc     240
atcatccacg accccgcgac cgactccctc gtcggcgact cctttgacat cgccgcctac     300
ctgcagcgca cgtatcccgc ctcgggcgcc ggcgacctct ccccccccca gaagctcgac     360
tacgcagtcg gcagggacat gccgcagctg ctcatcccgc tgtccgagat tcgcgcatca     420
ccagagctcg cagactacgc ccgcttcaac agcaacgttg acgtagcctt taccgcgcac     480
gtgggcctca tggtccacgg acttcccttg gatcctgcca ccgccgacgt gaccaaggcc     540
gagtttgtgc ggcgcgcggg gctctcatcg tgggacgact tggaaatggt tggcgaggcg     600
cgcgacaaga tgatgcagtc cctccgaaac atgctggggg acctggctgc cttgtttcgg     660
aaagatgcga gcgggccgtt cctgttgggg cagagggcca cgtatgcgga catgattgtc     720
ggtggctggt tgcgcatgat gcgggcgacg ttgccggtga gtgagtggca ggaggcgaga     780
gcctgccacg gagctatctt tgggcagctg catgatgcgc tggacaagta tgccgaggtg     840
aagtag                                                                846

<210> SEQ ID NO 22
<211> LENGTH: 846
<212> TYPE: DNA
<213> ORGANISM: Thinopyrum ponticum

<400> SEQUENCE: 22
atggccacct ccgcctccac ctccacccca atcatcttct acgacatagc ccagcggccc      60
cccgtcgcag aaacatgctg cgccgtcaac ccttggaaat ccagactggc cctcaacttc     120
aaggccgtcc cctacacaac cacctgggtg aagatgccag acatcagcag cgtccgcgcc     180
agcctcaacg tgccagcgtg tcgcaagttc gccgacggct ccgacttcaa caccctgccc     240
atcatccacg accccgcgac cgactccctc gtcggcgact cctttgacat cgccgcctac     300
ctgcagcgca cgtatcccgc ctcgggcgtc ggcgacctct ccccccccca gaagctcgac     360
tacgcagtcg gcagggacat gccgcagctg ctcatcccgc tgtccgagat tcgcgcatca     420
ccagagctcg cagactacgc ccgcttcaac agcaacgttg acgcagcctt taccgcgcac     480
gtgggcctca tggtccacgg acttcccttg gatcctgcca ccgccgacgt gaccaaggcc     540
gagtttgtgc ggcgcgcggg gctctcatcg tgggacgact tggaaatggt tggcgaggcg     600
cgcgacaaga tgatgcagtc cctccgaaac atgctggggg acctggctgc cttgtttcgg     660
aaagatgcga gcgggccgtt cctgttgggg cagagggcca cgtatgcgga catgattgtc     720
ggtggctggt tgcgcatgat gcgggcgacg ttgccggtga gtgagtggca ggaggcgaga     780
gcctgccacg gagctatctt tgggcagctg catgatgcgc tggacaagta tgccgaggtg     840
aagtag                                                                846

<210> SEQ ID NO 23
<211> LENGTH: 846
<212> TYPE: DNA
<213> ORGANISM: Thinopyrum ponticum
```

```
<400> SEQUENCE: 23
atggccacct ccgcctccac ctccacccca atcatcttct acgacatagc ccagcggccc     60
cccgtcgcag aaacatgctg cgccgtcaac ccttggaaat ccagactggc cctcaacttc    120
aaggccgtcc cctacacaac cacctgggtg aagatgccag acatcagcag cgtccgcgcc    180
agcctcaacg tgccagcgtg tcgcaagttc gccgacggct ccgacttcaa caccctgccc    240
atcatccacg accccgcgac cgactccctc gtcggcgact cctttgacat cgccgcctac    300
ctgcagcgca cgtatcccgc ctcgggcgcc ggcgacctct ccccccccca gaagctcgac    360
tacgcagtcg gcagggacat gccgcagctg ctcatcccgc tgtccgagat tcgcgcatca    420
ccagagctcg cagactacgc ccgcttcaac agcaacgttg acgcagcctt taccgcgcac    480
gtgggcctca tggtccacgg acttcccttg gatcctgcca ccgccgacgt gaccaaggcc    540
gagtttgtgc ggcgcgcggg gctctcatcg tgggacgact tggaaatggt tggcgaggcg    600
cgcgacaaga tgatgcagtc cctccgaaac atgctggggg acctggctgc cttgtttcgg    660
aaagatgcga gcgggccgtt cctgttgggg cagagggcca cgtatgcgga catgattgtc    720
ggtggctggt tgcgcatgat gcgggcgatg ttgccggtga gtgagtggca ggaggcgaga    780
gcctgccacg gagctatctt tgggcagctg catgatgcgc tggacaagta tgccgaggtg    840
aagtag                                                              846

<210> SEQ ID NO 24
<211> LENGTH: 846
<212> TYPE: DNA
<213> ORGANISM: Thinopyrum ponticum

<400> SEQUENCE: 24
atggccacct ccgcctccac ctccacccca atcatcttct acgacatagc ccagcggccc     60
cccgtcgcag aaacatgctg cgccgtcaac ccttggaaat ccagactggc cctcaacttc    120
aaggccgtcc cctacacaac cacctgggtg aagatgccag acatcagcag cgtccgcgcc    180
agcctcaacg tgccagcgtg tcgcaagttc gccgacggct ccgacttcaa caccctgccc    240
atcatccacg accccgcgac cgactccctc gtcggcgact cctttgacat cgccgcctac    300
ctgcagcgca cgtatcccgc ctcgggcgcc ggcgacctct ccccccccca gaagctcgac    360
tacgcagtcg gcagggacat gccgcagctg ctcatcccgc tgtccgagat tcgcgcatca    420
ccagagctcg cagactacgc ccgcttcaac agcaacgttg acgcagcctt taccgcgcac    480
gtgggcctca tggtccacgg acttcccttg gatcctgcca ccgccgacgt gaccaaggcc    540
gagtttgtgc ggcacgcggg gctctcatcg tgggacgact tggaaatggt tggcgaggcg    600
cgcgacaaga tgatgcagtc cctccgaaac atgctggggg acctggctgc cttgtttcgg    660
aaagatgcga gcgggccgtt cctgttgggg cagagggcca cgtatgcgga catgattgtc    720
ggtggctggt tgcgcatgat gcgggcgacg ttgccggtga gtgagtggca ggaggcgaga    780
gcctgccacg gagctatctt tgggcagctg catgatgcgc tggacaagta tgccgaggtg    840
aagtag                                                              846

<210> SEQ ID NO 25
<211> LENGTH: 843
<212> TYPE: DNA
<213> ORGANISM: Epichloe bromicola
```

-continued

<400> SEQUENCE: 25

```
atggccacct ccacctccat ctccacccca atcatcttct acgacatagc ccagcggccc      60
cccgtgacag aaacatgctg cgccgtcaac ccttggaaat ccagactggc cctcaacttc     120
aaggccgtcc cctacacaac cacctgggtc aagatgccag acatcagcag cgtccgcgcc     180
agcctcaacg tgccagcgtg tcgcaaattc gccgacggct ccgacttcaa caccctgccc     240
atcatccacg accccgcgac cgactccctc gtcggcgact ccttcgacat cgccgcctac     300
ctgcagcgca cgtatcccgc ctccggcgcc ggcgacctct ttcccccca gaagctcgac      360 tacgcagtcg gcagggacat gcagctgctc atcccgctgt ccgagactcg ggcatcccca     420
gagcttgcag actacgcccg cttcaacagc aacgttgacg cagcctttac cgcacacgtg     480
ggcctcatgg tccacgggct tcccttggat cctgccaccg cggacgtgac caaggccgag     540
tttgtgcggc gcgcgggggt ctcgtcgtgg gaggacttcg aaatggttgg tgaggcgcgc     600
gagaagatga tgcagtccct ccggaacatg ctggggacc tggctgcctt gttccggaga      660
gatgcgagcg gccgttctt gctgggacag aaggccacct atgcggatct gattgtcggt      720
ggctggctgc ggatgatgcg ggcgacgttg ccggcgagtg agtggcagga ggtgagagcc     780
tgccacgggg ctgtcttcgg caactgcat gatgcgctgg acaagtatgc cgaggtgaag      840
tag                                                                    843
```

<210> SEQ ID NO 26
<211> LENGTH: 840
<212> TYPE: DNA
<213> ORGANISM: Epichloe amarillans

<400> SEQUENCE: 26

```
atggccacct ccacctccac cccaatcatc ttctacgaca tagcccagcg gcccccgtc       60 acagaaacgt gctgcgccgt caacccttgg aaatccagac tggccctcaa cttcaaggcc     120
gtcccctaca caaccacctg ggtcaagatg ccagacatca gcagcgtccg cgccagcctc     180
aacctgccag cgtgtcgcaa gttcgccgac ggcaccgact tcgacaccct gcccatcatc     240
cacgaccccg cgaccggctc cctcatcggc gactccttcg acatcgccgc ctacctgcag     300
cgcacgtatc ccgcctccgg cgccggcgac ctcttccccc cccagaagct cgactacgcc     360
gccggcaggg acacgcagct gctcatcccg ctgtccgagg ttcgcgccgc atccccggag     420
ctcgcagact acgcccgctt caacagcaac gttgacgcag ccttcaccgc gcacgtgggc     480
ctcatggtcc acgggcttcc cttggaccct gccaccgcgg acgtgaccaa ggccgagttt     540
gtgcggcgcg cggccgtctc atcgtgggac gacctcgaca tggttggcga cgcgcgcgac     600
aagatgatgc agtccctccg gaacacgctg ggggacctgg ccgccttgtt tcggagagat     660
gcgagcgggc cgttcttgct gggacccaag gccacgtacg cggatctgat tgtcggtggc     720
tggttgcgca tgatgcgggc gacgttgccg ccgagtgagt ggcaggcggc gagagcttgg     780
cacggggctg tcttcgggca gctgcatgat gcgctggaca agtacgccga ggtgaagtag     840
```

<210> SEQ ID NO 27
<211> LENGTH: 795
<212> TYPE: DNA
<213> ORGANISM: Epichloe baconii -continued

<400> SEQUENCE: 27
atggccacct ccacctccac ctccacctcc acctccaccc caatcatctt ctacgacata      60
gcccagcggc cccccgtcac agaaacatgc tgcgccgtca acccttggaa atccagactg     120
gccctcaact tcaaggccgt ccctacaca accacctggg tcaagatgcc cgacatcagc      180
agcgtccgcg ccagcctcaa cctgccagcg tgtcgcaagt cgccgacgg caccgacttc      240 aacaccctgc ccatcatcca cgaccccgcg accggctccc tcgtcggcga ctccttcgac     300
atcgccgcct acctgcagcg cacggacacg cagctgctca tcccgctgtc cgaggttcgc     360
gccgcatcct cggacctcgc agactacgcc cgcttcaaca gcaacgttga cgcagccttt     420
accgcgcacg tgggcctcat ggtccacggg cttcccttgg accctgccac cgcggacgtg     480
accaaggccg agtttgtgcg gcgcgcgggg gtctcatcgt gggacgactt cgagatggca     540
ggcgaggcgc gcgagaagat gatgcagtcc ctccggaaca cgctgggggga cctggccgcc    600 ttgtttcgga gagatgcgag cgggccgttc ttgctgggac gcaaggccac gtacgcggat     660
ctgattgtcg gtggctggtt gcgcatgatg cgggcgacgt tgccggcgag tgagtggcag     720
gcggcgagag cttggcacgg ggctgtcttc gggcagctgc atgatgcgct ggacaagtat     780
gccgaggtga agtag                                                       795

<210> SEQ ID NO 28
<211> LENGTH: 861
<212> TYPE: DNA
<213> ORGANISM: Epichloe festucae

<400> SEQUENCE: 28
atggccacct ccacctccac ctccacctcc accccaatca tcttctacga catagcccag      60 cggcccccg tcacagaaac atgctgcgcc gtcaacccctt ggaaaaccag actggccctc     120
aacttcaagg ccgtcaccta cacaaccacc tgggtcaaga tgccagacat cagcggcgtc     180
cgcgccagcc tcaacgtgcc agcgtgtcgc aaattcgccg acggcaccga cttcaacacc     240
ctgcccatca tccacgaccc cgcgaccggc tccctcatcg gcgactcctt cgacatcgcc     300
gcctacctgc agcgcaccta tcccgcctcc ggcgctggcc acctcttccc cccccttccc     360 cccctcaga agctcgacta cgccgtcggc agggacatgc agctgctcat cccgctgtcc      420
gaggttcgcg catcctcgga gctcgcagac tacgcccgct tcaacagcaa cgttgacgca     480
gcctttaccg cgcacgtcgg cgtcatggtc cacgggcttc ccttggatcc tgccaccgcg     540
gacgtgacca aggccgagtt cgtgcggcgc gcggggggtct catcgtggga ggacttcgaa     600
atggtcggtg aggcgcgcga agatgatg cagtccctcc ggaacatgct gggggacctg       660
gccgccttgt ttcggagaga tgcgagcggg ccgttcttgc tgggacagca ggccacgtac     720
gcggatctga ttgtcggtgg ctggttgcgc atgatgcggg cgacgttgcc ggccagtgag     780
tggcaggagg tgagagcttg gcacggggct gtcttcgggc ggctgcatga tgcgctggac     840
aagtatgccg aggtgaagta g                                                861

<210> SEQ ID NO 29
<211> LENGTH: 846
<212> TYPE: DNA
<213> ORGANISM: Epichloe gansuensis

```
<400> SEQUENCE: 29
atggccacct ccacctccac ttccgcctcc accccaatca tcttctacga catagcccag      60 cgccccccg tcacagaaac atgctgcgcc gtcaaccctt ggaaatccag actggccctc      120
aatttcaagg ccgtcccta cacaaccacc tgggtcgaga tgccagacat cagcagcgtc      180
cgcgccagtc tcaacctgcc agcgtgtcgc aaattcgccg acggctccga cttcaatacc      240
ctgcccatca tccacgaccc cgcgaccggc tccctcatcg gcgactcctt cgacatcgcc      300
gcctacctgc agcgcacgta tcccgcctcg ggcgccgacg acctcttccc cccccagaag      360
ctggactacg tagtcggcag ccatgtccag ccgttcatcc cgctgtctga cattcgcgca      420
tcagagtttg cagattacgc ccgcttcaac agcaacgttg acgcagcctt taccgcacac      480
gtgggcctca tgctccacgg acttcccttg gatcctgcca ccgcggacgt gaccaaggca      540
gaattcgtgc gacgcgccgg ggtctcgtcg tgggaggatt ttgaaatggt tggtgaggcg      600
cgggagaaga tgatgcagtc ctttcggact atgctggagg acctggctgc cttgttccgg      660
agagatgcga ccgggccgtt cttgctggga cagaaggcta cgtatgcgga tctgattgtc      720
ggcgggtggt tgcggatgat gcgcgcgacg ttgccggcga gtgagtggca ggaggcgaga      780
gcttggcatg gggccgtctt cggacaactg catgatgcgc tggacaagta tgccgaggtg      840
aagtag                                                                 846

<210> SEQ ID NO 30
<211> LENGTH: 846
<212> TYPE: DNA
<213> ORGANISM: Epichloe typhina

<400> SEQUENCE: 30
atggccacct cctccacctc cacctccacc ccaatcatct tctacgacat agcccagcgg      60
ccccccgtcg cagaaacatg ctgcgccgtc aacccttgga aatccagact ggccctcaac      120
ttcaaggccg tccctacac aaccacctgg gtcaagatgc cagacatcag cagcgtccgc      180
gccagcctca cgtgccagc gtgtcgtaaa ttcgccgacg gctccgactt caacaccctg      240
cccatcatgc acgaccccgc gaccgactcc ctcatcggcg actccttcga tatcgccgcc      300
tacctgcagc gcacgtatcc cgcctccggc gccggcgacc tcttccccc ccagaagctc      360 gactacgcag tcggcaggga catgcagctg ctcatcccgc tgtccgaggt ccgcgcatca      420
ccagagctcg cagactacgc ccgcttcaac agcaacgttg acgcagcctt taccgcgcac      480
gtgggcctca tggtccacgg gcttcccttg gatcctgcca ccgcagacgt gaccaaggcc      540
gagtttgtgc ggcgcgcggg ggtctcgtcg tgggaggact tcgaaatggt tggcgaggtg      600
cgcgagaaga tgatgcagtc cctccggaac atgctcgggg acctggctgc cttgtttcgg      660
agagatgcga gcgggccgtt cctgctgggg cagagggcca cgtatgcgga cctgattgtc      720
ggtggctggt tgcgcatgat gcgcgcgacg ttgccggcga gtgagtggca ggaggcgaga      780
gcctgccacg gggccatctt cgggcagctg catgatgcgc tggacaagta tgccgaggtg      840
aagtag                                                                 846

<210> SEQ ID NO 31
<211> LENGTH: 846
<212> TYPE: DNA
<213> ORGANISM: Epichloe uncinata
```

```
<400> SEQUENCE: 31
atggccacct cctccacctc cacctccacc ccaatcatct tctacgacat agcccagcgg      60 cccccgtcg cagaaacatg ctgcgccgtc aacccttgga aatccagact ggccctcaac     120
ttcaaggccg tcccctacac aaccacctgg gtcaagatgc cagacatcag cagcgtccgc     180
gccagcctca acgtgccagc gtgtcgtaaa ttcgccgacg gctccgactt caacaccctg     240
cccatcatgc acgaccccgc gaccgactcc ctcatcggcg actccttcga catcgccgcc     300
tacctgcagc gcacgtatcc cgcctccggc gccggcgacc tcttccccc ccagaagctc     360 gactacgcag tcggcaggga catgcagctg ctcatcccgc tgtccgaggt ccgcgcatca     420
ccagagctcg cagactacgc ccgcttcaac agcaacgttg acgcagcctt taccgcgcac     480
gtgggcctca tggtccacgg gcttcccttg gatcctgcca ccgcggacgt gaccaaggcc     540
gagtttgtgc ggcgcgcggg ggtctcgtcg tgggaggact cgaaatggt tggcgaggtg      600 cgcgagaaga tgatgcagtc cctccggaac atgctcgggg acctggctgc cttgtttcgg     660
agagatgcga gcgggccgtt cctgctgggg cagagggcca cgtatgcgga cctgattgtc     720
ggtggctggt tgcgcatgat gcgcgcgacg ttgccggcga gtgagtggca ggaggcgaga     780
gcctgccacg gggccatctt cgggcagctg catgatgcgc tggacaagta tgccgaggtg     840
aagtag                                                                846

<210> SEQ ID NO 32
<211> LENGTH: 843
<212> TYPE: DNA
<213> ORGANISM: Epichloe sylvatica

<400> SEQUENCE: 32
atgaccacct ccacctccac ctccacccca atcatcttct acgacatagc ccagcggccc      60
cccgtcgcag aaacatgctg cgccgtcaac ccttggaaat ccagactggc cctcaacttc     120
aaggccgtcc cctacaaaac cacctgggtc aagatgccag acatcagcag cgtccgcgcc     180
agcctcaagg tgccagcgtg tcgtaaattc gccgacggct ccgacttcaa caccctgccc     240
atcatgcacg accccgcgac cgactccctc ctcggcgact ccttcgacat cgccgcctac     300
ctgcagcgca cgtatcccgc ctccggcgcc ggcgacctct cccccccca gaagctcgac     360 tacgcagtcg gcagggacat gcagctgctc atcccgctgt ccgaggtccg cgcgtcacca     420
gagctcgcag actacgcccg cttcaacagc aacgttgacg cagcctttac cgcgcacgtg     480
ggcctcatgg tccacgggct tcccttggat cctgcaccg cggacgtgac caaggccgag     540
tttgtgcggc gcgggggt ctcgtcgtgg gaggaccttg aaatggttgg cgaggcgcgc      600
gagaagatga tgcagtccct ccggaacatg ctcggggacc tggctgcctt gtttcggaga     660
gatgcgagcg gccgttcct gctggggcag agggccacgt atgcggacct gattgtcggt     720
ggctggttgc gcatgatgcg cgcgacgttg ccggcgagtg agtggcagga ggcgagagcc     780
tgccacgggg ccatcttcgg gcagctgcat gatgcgctgg acaagtatgc cgaggtgaag     840
tag                                                                   843

<210> SEQ ID NO 33
<211> LENGTH: 843
<212> TYPE: DNA
<213> ORGANISM: Epichloe aotearoae
```

```
<400> SEQUENCE: 33
atggccaccc ccacctccac ctccacccca atcatcttct acgacatagc ccagcggccc      60
cccgtcgcag aaacatgctg cgccgtcaac ccttggaaat ccagactggc cctcaacttc     120
aaggccgtcc cctacacaac cacctgggtc aagatgccag acatcagcag cgtccgcgcc     180
agcctcaacg tgccagcgtg tcgcaagttc gccgacggct ccgacttcaa caccctgccc     240
atcatgcacg accccgcgac ctcttccctc atcggcgact ccttcgacat cgccgcctac     300
ctgcagcgca cgtatcccgc ctcgggcgcc ggcgacctct ccccctccca gaagctcgac     360
tacgcagtcg ccagggacac gcagctgctc atcccgctgt ccgagattcg cgcatcatca     420
gagctcgcag actacgcccg cttcaacagc aacgttgacg cagcctttac cgcgcacgtg     480
ggcctcatgg tccacgggct tcccttggat cctgccaccg ccgacgtgac caaggccgag     540
tttgtgcggc gcgcgggcgt ctcatcgtgg gaggacttcg aaatggttgg cgaggcgcgc     600
gagaagatga tgcagtccct ccggaacatg ctggggacc tggctgcctt gtttcggaga     660
gatgcgagcg ggccgttcct gctggggcag agggccacgt atgcggacct gattgtcggt     720
ggctggttgc gcatgatgcg ggcgacgttg ccggcgagtg agtggcagga ggcgagagcc     780
tgccacgggg ctatcttcgg gcagctgcat gatgcgctgg acaagtatgc cgaggtgaag     840
tag                                                                    843

<210> SEQ ID NO 34
<211> LENGTH: 828
<212> TYPE: DNA
<213> ORGANISM: Epichloe glyceriae

<400> SEQUENCE: 34
atggccacct ccaccccaat catcttctac gacatagccc agcggcccc cgtcgcagaa       60 acatgctgcg ccgtcaaccc ttggaaatcc agactggccc tcaacttcaa ggccgtcccc     120
tacacaacca cctgggtcag catgccagac atcagcagcg tccgcgccag cctcaacgtg     180
ccggcgtgtc gcaaattcgc cgacggctcc gacttcaaca ccctgcccat catccacgac     240
cccgcgaccg gctccctcat cggcgactcc ttcgacatcg ccgcccacct gcagcgcgcc     300
tatcccgcct ccggcgccgg cgacctcttc cccccccagg agctggacta cgtggtcgcc     360
agggacacgc ggctgctcgt cccgctgtcc gagactcgcg catcagagtt cgcggactac     420
gcccgcttca acagcaacgt tgacgcagcc tttaccgcac acgtgggcct catggtccac     480
gggcttccct tggaccctgc caccgcggac gtgaccaagg cggagtttgt gcggcgcgcg     540
ggagtctcgt cgtgggagga tttcgaattg gttggtgagg cgcgcgagaa gatgatgcag     600
tccctccgga acgtgctggg ggacctggct gccttgtttc ggagagatgc gagcgggccg     660
ttcttgctgg gacagaaggc cacgtatgcg gatctgattg tcggtggctg gttgcggatg     720
atgcgggcga cgttgcccgc gagtgagtgg caggaggcga gagcctggca tggcgctgtc     780
ttcgggcagc tgcatgatgc gctggacaag tatgccgagg tgaagtag                  828

<210> SEQ ID NO 35
<211> LENGTH: 843
<212> TYPE: DNA
<213> ORGANISM: Epichloe brachyelytri
```

-continued

<400> SEQUENCE: 35

```
atggccacct ccacctccac ctccacccca atcatcttct acgacatagc ccagcggccc        60
cccgtcacag aaacatgctg cgccgtcaac ccttggaaat ccagactggc cctcaacttc       120
aaggccgtcc cctacacaac cacctgggtc aagatgccag acatcagcag cgtccgcgcc       180
agcctcaacg tgcctgcgtg tcgcaaattc gccgacggct ccgacttcaa caccctgccc       240
atcatccacg accccgcgac cgactccctc atcggcgact ccttcgacat cgccgcctac       300
ctgcagcgca cgtatcccgc ctccggcgcc ggcgacctct ccccccccca gaagctcgac       360
tacgcagtca gcagggacat gcagctgctc atcccgctgt ccgagatgcg cgcatcatca       420
gagctcgcag actacgcccg cttcaacagc aacgttgacg cagcctttac cgcgcacgtg       480
ggcctcatgg tccacgggct tcccttggat cctgccaccg cggacgtgac caaggccgag       540
tttgtgcggc gcgcgggggt ctcatcgtgg gaggatttcg aaatggttgg tgaggcgcgc       600
gagaagatga tgcagtccct ccggaacatg ctgggggacc tggctgcctt gtttcggaga       660
gatgcgagcg ggccgttctt gctggggcag aaggccacgt atgcggatct gattgtcggt       720
ggctggttgc gcatgatgcg ggcgacgttg ccggcgagtg agtggcagga ggtgagagcc       780
tggcacgggg ctatcttcgg gcagctgcat gatgcgctgg acaagtatgc cgaggtgaag       840
tag                                                                    843
```

```
<210> SEQ ID NO 36
<211> LENGTH: 281
<212> TYPE: PRT
<213> ORGANISM: Elytrigia ponticum

<400> SEQUENCE: 36

Met Ala Thr Ser Ala Ser Thr Ser Thr Pro Ile Ile Pro Thr Ala Ile
1               5                   10                  15

Ala Gly Ala Pro Pro Val Ala Gly Thr Cys Cys Ala Val Ala Pro Thr
                20                  25                  30

Leu Ser Ala Leu Ala Leu Ala Pro Leu Ala Val Pro Thr Thr Thr Thr
            35                  40                  45

Thr Val Leu Met Pro Ala Ile Ser Ser Val Ala Ala Ser Leu Ala Val
        50                  55                  60

Pro Ala Cys Ala Leu Pro Ala Ala Gly Ser Ala Pro Ala Thr Leu Pro
65                  70                  75                  80

Ile Ile His Ala Pro Ala Thr Ala Ser Leu Val Gly Ala Ser Pro Ala
                85                  90                  95

Ile Ala Ala Thr Leu Gly Ala Thr Thr Pro Ala Ser Gly Ala Gly Ala
            100                 105                 110

Leu Pro Pro Pro Gly Leu Leu Ala Thr Ala Val Gly Ala Ala Met Pro
        115                 120                 125

Gly Leu Leu Ile Pro Leu Ser Gly Ile Ala Ala Ser Pro Gly Leu Ala
    130                 135                 140

Ala Thr Ala Ala Pro Ala Ser Ala Val Ala Ala Ala Pro Thr Ala His
145                 150                 155                 160

Val Gly Leu Met Val His Gly Leu Pro Leu Ala Pro Ala Thr Ala Ala
                165                 170                 175

Val Thr Leu Ala Gly Pro Val Ala Ala Ala Gly Leu Ser Ser Thr Ala
            180                 185                 190

Ala Leu Gly Met Val Gly Gly Ala Ala Ala Leu Met Met Gly Ser Leu
        195                 200                 205
```

Ala Ala Met Leu Gly Ala Leu Ala Ala Leu Pro Ala Leu Ala Ala Ser
   210               215                 220

Gly Pro Pro Leu Leu Gly Gly Ala Ala Thr Thr Ala Ala Met Ile Val
225               230             235             240

Gly Gly Thr Leu Ala Met Met Ala Ala Thr Leu Pro Val Ser Gly Thr
          245             250             255

Gly Gly Ala Ala Ala Cys His Gly Ala Ile Pro Gly Gly Leu His Ala
        260           265           270

Ala Leu Ala Leu Thr Ala Gly Val Leu
     275          280

<210> SEQ ID NO 37
<211> LENGTH: 40
<212> TYPE: DNA
<213> ORGANISM: Artificial Sequence
<220> FEATURE:
<223> OTHER INFORMATION: Synthesized

<400> SEQUENCE: 37
tgcagcccgg ggatccagaa atccacccat cgtcatcacc                                40

<210> SEQ ID NO 38
<211> LENGTH: 42
<212> TYPE: DNA
<213> ORGANISM: Artificial Sequence
<220> FEATURE:
<223> OTHER INFORMATION: Synthesized

<400> SEQUENCE: 38
acctgtaatt cacacgtgct acttcacctc ggcatacttg tc                             42

<210> SEQ ID NO 39
<211> LENGTH: 38
<212> TYPE: DNA
<213> ORGANISM: Artificial Sequence
<220> FEATURE:
<223> OTHER INFORMATION: Synthesized

<400> SEQUENCE: 39
acatgattac gaattcttct actagtgccc cacctacg                                  38

<210> SEQ ID NO 40
<211> LENGTH: 41
<212> TYPE: DNA
<213> ORGANISM: Artificial Sequence
<220> FEATURE:
<223> OTHER INFORMATION: Synthesized

<400> SEQUENCE: 40
acctgtaatt cacacgtgcg accagccagg aaacaccact g                              41

<210> SEQ ID NO 41
<211> LENGTH: 20
<212> TYPE: DNA
<213> ORGANISM: Artificial Sequence
<220> FEATURE:
<223> OTHER INFORMATION: Synthesized

<400> SEQUENCE: 41
tgcagtccct ccgaaacatg                                                      20

<210> SEQ ID NO 42
<211> LENGTH: 22

<212> TYPE: DNA
<213> ORGANISM: Artificial Sequence
<220> FEATURE:
<223> OTHER INFORMATION: Synthesized

<400> SEQUENCE: 42
caaatggacg aacggataaa cc                                        22

<210> SEQ ID NO 43
<211> LENGTH: 22
<212> TYPE: DNA
<213> ORGANISM: Artificial Sequence
<220> FEATURE:
<223> OTHER INFORMATION: Synthesized

<400> SEQUENCE: 43
agcggaaaca cgcatctgac ct                                        22

<210> SEQ ID NO 44
<211> LENGTH: 22
<212> TYPE: DNA
<213> ORGANISM: Artificial Sequence
<220> FEATURE:
<223> OTHER INFORMATION: Synthesized

<400> SEQUENCE: 44
ttacccgcca atatatcctg tc                                        22

<210> SEQ ID NO 45
<211> LENGTH: 24
<212> TYPE: DNA
<213> ORGANISM: Artificial Sequence
<220> FEATURE:
<223> OTHER INFORMATION: Synthesized

<400> SEQUENCE: 45
tgattcttct tccgtttcta agga                                      24

<210> SEQ ID NO 46
<211> LENGTH: 22
<212> TYPE: DNA
<213> ORGANISM: Artificial Sequence
<220> FEATURE:
<223> OTHER INFORMATION: Synthesized

<400> SEQUENCE: 46
atgtcaaagg agtcgccgac ga                                        22

<210> SEQ ID NO 47
<211> LENGTH: 25
<212> TYPE: DNA
<213> ORGANISM: Artificial Sequence
<220> FEATURE:
<223> OTHER INFORMATION: Synthesized

<400> SEQUENCE: 47
ttcatcatcc tgctaggcga taaga                                     25

<210> SEQ ID NO 48
<211> LENGTH: 26
<212> TYPE: DNA
<213> ORGANISM: Artificial Sequence
<220> FEATURE:
<223> OTHER INFORMATION: Synthesized -continued

```
<400> SEQUENCE: 48
ctacttcacc tcggggcata cttgtc                                    26

<210> SEQ ID NO 49
<211> LENGTH: 32
<212> TYPE: DNA
<213> ORGANISM: Artificial Sequence
<220> FEATURE:
<223> OTHER INFORMATION: Synthesized

<400> SEQUENCE: 49
ccatggctag aaatccaccc atcgtcatca cc                             32

<210> SEQ ID NO 50
<211> LENGTH: 28
<212> TYPE: DNA
<213> ORGANISM: Artificial Sequence
<220> FEATURE:
<223> OTHER INFORMATION: Synthesized

<400> SEQUENCE: 50
ggatcctctt cacctcggca tacttgtc                                  28

<210> SEQ ID NO 51
<211> LENGTH: 34
<212> TYPE: DNA
<213> ORGANISM: Artificial Sequence
<220> FEATURE:
<223> OTHER INFORMATION: Synthesized

<400> SEQUENCE: 51
attattcgaa agaaatccac ccatcgtcat cacc                           34

<210> SEQ ID NO 52
<211> LENGTH: 34
<212> TYPE: DNA
<213> ORGANISM: Artifical Sequence
<220> FEATURE:
<223> OTHER INFORMATION: Synthesized

<400> SEQUENCE: 52
ttgttctaga ctacttcacc tcggcatact tgtc                           34
```